United States Patent
Juminaga et al.

(10) Patent No.: US 9,540,652 B2
(45) Date of Patent: Jan. 10, 2017

(54) METABOLIC ENGINEERING OF THE SHIKIMATE PATHWAY

(75) Inventors: Darmawi Juminaga, Albany, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 305 days.

(21) Appl. No.: 14/342,335

(22) PCT Filed: Aug. 31, 2012

(86) PCT No.: PCT/US2012/053547
§ 371 (c)(1),
(2), (4) Date: Oct. 28, 2014

(87) PCT Pub. No.: WO2013/033652
PCT Pub. Date: Mar. 7, 2013

(65) Prior Publication Data
US 2015/0044734 A1 Feb. 12, 2015

Related U.S. Application Data

(60) Provisional application No. 61/530,901, filed on Sep. 2, 2011.

(51) Int. Cl.
| | | |
|---|---|---|
| C12N 15/70 | (2006.01) | |
| C12N 9/88 | (2006.01) | |
| C12N 15/52 | (2006.01) | |
| C12P 7/42 | (2006.01) | |

(Continued)

(52) U.S. Cl.
CPC .............. *C12N 15/70* (2013.01); *C12N 9/001* (2013.01); *C12N 9/88* (2013.01); *C12N 15/52* (2013.01); *C12P 7/42* (2013.01); *C12P 13/22* (2013.01); *C12P 13/225* (2013.01); *C12P 13/227* (2013.01);
(Continued)

(58) Field of Classification Search
CPC ........... C12N 15/70; C12N 9/88; C12N 15/52; C12P 7/42; Y02P 20/52
See application file for complete search history.

(56) References Cited

U.S. PATENT DOCUMENTS

| | | | |
|---|---|---|---|
| 6,210,937 B1 * | 4/2001 | Ward ..................... | C12N 15/52 435/146 |
| 2007/0087424 A1 * | 4/2007 | Frost .................... | C12N 9/0006 435/146 |
| 2008/0102499 A1 | 5/2008 | Templeton et al. | |

FOREIGN PATENT DOCUMENTS

WO    WO/2010/141468    * 9/2010

OTHER PUBLICATIONS

Gosset et al. Production of aromatic compounds in bacteria., Current Opinion in Biotechnology (2009), vol. 20, pp. 651-658.*

(Continued)

*Primary Examiner* — Alexander Kim
(74) *Attorney, Agent, or Firm* — Richard Aron Osman

(57) ABSTRACT

The present disclosure relates to engineered microorganisms that produce amino acids and amino acid intermediates. In particular, the disclosure relates to recombinant nucleic acids encoding operons that increase production of aromatic amino acids and the aromatic amino acid intermediate shikimate; microorganisms with increased production of aromatic amino acids and the aromatic amino acid intermediate shikimate; and methods related to the production of aromatic amino acids, the aromatic amino acid intermediate shikimate, and commodity chemicals derived therefrom.

27 Claims, 4 Drawing Sheets

(51) Int. Cl.
*C12P 13/22* (2006.01)
*C12N 9/02* (2006.01)

(52) U.S. Cl.
CPC ...... *C12Y 103/01012* (2013.01); *C12Y 401/02* (2013.01); *Y02P 20/52* (2015.11)

(56) References Cited

OTHER PUBLICATIONS

Ikeda, Towards bacterial strain overproducing L-tryptophan and other aromatics by metabolic engineering., Appl Microbiol Biotehcnol (2006), vol. 69, pp. 615-626.*
Kramer et al., Metabolic engineering for microbial production of shikimic acid., Metabolic Engineering (2003), vol. 5, pp. 277-283.*
Ran et al. Directed Evolution of 2-keto-3-deoxy-6-phosphogalactonate Aldolase to Replace 3-Deoxy-D-arabino-heptulosonic Acid 7-Phosphate Synthase, JACS (2007), vol. 129, pp. 6130-6139.*
Sprenger, From scratch to value: engineering *Escherichia coli* wild type cells to the production of L-phenylalanine and other fine chemicals derived from chorismate., Appl Microbiol Biotechnol. (2007), vol. 75(4), pp. 739-749.*
Yi et al., Modulation of phosphoenolpyruvate synthase expression increases shikimate pathway product yields in *E. coli.*, Biotechnol Prog. (2002), vol. 18(6), pp. 1141-1148.*
International Search Report and Written Opinion received for PCT Patent Application No. PCT/US2012/053547, mailed on Dec. 14, 2012, 18 pages.
International Preliminary Report on Patentability received for PCT Patent Application No. PCT/US2012/053547, mailed on Mar. 13, 2014, 12 pages.
Báez-Viveros et al., "Metabolic Transcription Analysis of Engineered *Escherichia coli* Strains that Overproduce L-Phenylalanine", Microbial Cell Factories, vol. 6, No. 30, 2007: 20 pages.
Chandran et al., "Phosphoenolpyruvate Availability and the Biosynthesis of Shikimic Acid", Biotechnology Progress, vol. 19, No. 3, 2003, pp. 808-814.
Chávez-Béjar et al., "Metabolic Engineering of *Escherichia coli* for L-Tyrosine Production by Expression of Genes Coding for the Chorismate Mutase Domain of the Native Chorismate Mutase-Prephenate Dehydratase and a Cyclohexadienyl Dehydrogenase from Zymomonas Mobilis", Applied and Environmental Microbiology, vol. 74, No. 10, May 2008, pp. 3284-3290.
Chen et al., "Deletion of the Arok Gene is Essential for High Shikimic Acid Accumulation through the Shikimate Pathway in *E. coli*". Bioresource Technology, vol. 119, 2012, pp. 141-147.
Escalante et al., "Metabolic Engineering for the Production of Shikimic Acid in an Evolved *Escherichia coli* Strain Lacking the Phosphoenolpyruvate: Carbohydrate Phosphotransferase System", Microbial Cell Factories, vol. 9, No. 21, 2010, 12 pages.
Gosset, Guillermo, "Production of Aromatic Compounds in Bacteria", Current Opinion in Biotechnology, vol. 20, Dec. 2009, pp. 651-658.
Johansson et al., "Shikimic Acid Production by a Modified Strain of *E. coli.* (W3110.Shik1) under Phosphate-Limited and Carbon-Limited Conditions", Biotechnology and Bioengineering, vol. 92, No. 5, Dec. 2005, pp. 541-552.
Juminaga et al., "Modular Engineering of L-Tyrosine Production in *Escherichia coli*", Applied and Environmental Microbiology, vol. 78, No. 1, Jan. 2012, pp. 89-98.
Lütke-Eversloh et al., "Combinatorial Pathway Analysis for Improved L-Tyrosine Production in *Escherichia coli*: Identification of Enzymatic Bottlenecks by Systematic Gene Overexpression": Metabolic Engineering, vol. 10, 2008: pp. 69-77.
Lütke-Eversloh et al., "L-Tyrosine Production by Deregulated Strains of *Escherichia Coli*", Applied Microbiology and Biotechnology, vol. 75, 2007, pp, 103-110.
Patnaik et al., "Pathway Engineering for Production of Aromatics in *Escherichia coli*: Confirmation of Stoichiometric Analysis by Independent Modulation of AroG: TktA, and Pps Activities", Biotechnology and Bioengineering, vol. 46: No. 4, May 1995, pp. 361-370.
Rizk et al., "Ensemble Modeling for Aromatic Production in *Escherichia coli*",.PLoS One, vol. 4, No. 9, Sep. 2009, pp. e6903 (1-14).
Shen et al., "Improved Production of Tryptophan in Genetically Engineered *Escherichia coli* with TktA and PpsA Overexpression", Journal of Biomedicine and Biotechnology, vol. 2012, Article ID 605219, 2012, pp. 1-8.
Yi et al., "Altered Glucose Transport and Shikimate Pathway Product Yields in *E. coli*", Biotechnology Progress: vol. 19, No. 5, 2003, pp. 1450-1459.

* cited by examiner

METABOLIC ENGINEERING OF THE SHIKIMATE PATHWAY

CROSS-REFERENCE TO RELATED APPLICATIONS

This is a U.S. National Phase patent application of PCT/US2012/053547, filed Aug. 31, 2012, which claims priority to U.S. Provisional Patent Application No. 61/530,901, filed Sept. 2, 2011, each of which is incorporated herein by reference in its entirety.

STATEMENT REGARDING FEDERALLY SPONSORED RESEARCH OR DEVELOPMENT

This disclosure was made with government support under contract DE-AC02-05CH11231 awarded by the U.S. Department of Energy, and under award EEC 0540879 from the National Science Foundation. The government has certain rights in the disclosure.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 416272009540SeqList.txt, date recorded: Aug. 30, 2012, size: 1 KB).

FIELD

The present disclosure relates to engineered microorganisms that produce amino acids and amino acid intermediates. In particular, the disclosure relates to recombinant nucleic acids encoding operons that increase production of aromatic amino acids and the aromatic amino acid intermediate shikimate; microorganisms with increased production of aromatic amino acids and the aromatic amino acid intermediate shikimate; and methods related to the production of aromatic amino acids, the aromatic amino acid intermediate shikimate, and commodity chemicals derived therefrom.

BACKGROUND

The traditional approach for improving microbial production of natural products, such as amino acids, antibiotics, etc., includes altering key structural or regulatory genes of the biosynthetic pathway followed by measuring the amount of desired product that is produced. Each change then reveals the presence or absence of a bottleneck and, based on those results, the next gene is deleted or overexpressed, and the cycle repeats until product titers/yields can no longer be improved substantially. Although this step-wise approach can yield improvements in flux through these pathways, it is a tedious and time-consuming strategy, given that metabolic pathways tend to be well balanced and rarely does a single change increase flux dramatically. Indeed, some bottlenecks will not be revealed until others are relieved. This process typically leads to the identification of local yield maxima, but not the global optimal yield.

These challenges are particularly evident in efforts to engineer *Escherichia coli* to produce high yields of aromatic amino acids. With advances in metabolic engineering and discovery of novel biosynthetic pathways in plants, aromatic amino acids, which have been important commodities used as animal feeds, food additives, and supplements, can also serve as precursors to a variety of commercially valuable molecules and pharmaceutical drugs (Gosset, G. *Curr Opin Biotechnol* 20:651-658, 2009; and Sprenger, G A. *Appl Microbiol Biotechnol* 75:739-749, 2007). It has recently been shown that L-tyrosine over-producing strains of *Escherichia coli* grown on glucose can be used to produce biopolymer starting materials such as p-hydroxycinnamic acid and p-hydroxystyrene, and drug precursors such as reticuline, an important intermediate in biosyntheses of benzylisoquinoline alkaloids (Minami, H J et al. *Proc Natl Acad Sci USA* 105:7393-7398, 2008; Sariaslani, F S et al. *Annu Rev Microbiol* 61:51-69, 2007; and Sato, F T et al. *Curr Pharm Biotechnol* 8:211-218, 2007). Yet, of the three aromatic amino acids derived from the shikimate pathway, the L-tyrosine yield has been shown to be the lowest. While L-tyrosine titers of over 50 g/L can be produced using *E. coli* in a 200-L bioreactor by improving the fermentation and isolation steps (Patnaik, R et al. Biotechnol Bioeng 99:741-752, 2008), the production strain only yielded about 0.10 gram of L-tyrosine per gram of glucose (Olson, M M et al. *Microbiol Biotechnol* 74:1031-1040, 2007). Accordingly, a need exists for further improvements in L-tyrosine yields to make the process as economically competitive as the processes used to synthesize other amino acids, such as L-lysine, L-glutamate, and L-alanine (Ikeda, M. *Appl Microbiol Biotechnol* 69:615-626, 2006; and Leuchtenberger, W et al. *Appl Microbiol Biotechnol* 69:1-8, 2005).

Another problem with increasing L-tyrosine yields is that despite a vast wealth of literature accumulated over the past thirty years pertaining to the enzymatic activities and expression properties of the shikimate pathway, the pathway remains difficult to engineer (Bongaerts, J et al. *Metab Eng* 3:289-300, 2001; Gosset, G. *Curr Opin Biotechnol* 20:651-658, 2009; Herrmann, K M and Weaver, L M. *Physiol Plant Mol Biol* 50:473-503, 1999; Ikeda, M. *Appl Microbiol Biotechnol* 69:615-626, 2006; and Sprenger, G A. *Appl Microbiol Biotechnol* 75:739-749, 2007). Previous L-tyrosine engineering work has most often focused on the transcriptional deregulation of the tyrR and/or trpR regulons, followed by removing the feedback inhibition on two key enzymes, 3-deoxy-D-arabino-heptulosonate (DAHP) synthase (AroG), which catalyzes the first committed step to the shikimate pathway, and the dual function chorismate mutase/prephenate dehydrogenase (TyrA), which catalyzes the first two steps in L-tyrosine biosynthesis from chorismate (Lutke-Eversloh, T and Stephanopoulos, G. *Appl Microbiol Biotechnol* 75:103-110, 2007; and Olson, M M et al. *Appl Microbiol Biotechnol* 74:1031-1040, 2007). Co-expression of the rate-limiting enzymes shikimate kinase (AroK or AroL) and quinate/shikimate dehydrogenase (YdiB), and deletion of the L-phenylalanine branch of the aromatic amino acid biosynthetic pathway have been shown to increase the L-tyrosine production (Gavini, N and Pulakat, L. *J Bacteriol* 173:4904-4907, 1991; Lutke-Eversloh, T and Stephanopoulos, G. *Appl Microbiol Biotechnol* 75:103-110, 2007; and Olson, M M et al. *Appl Microbiol Biotechnol* 74:1031-1040, 2007). Furthermore, overexpression of phosphoenolpyruvate synthase (PpsA) and transketolase A (TktA), altering glucose transport and use of other carbon sources, such as xylose and arabinose, have also been shown to increase the precursor pools to the shikimate pathway (Ahn, J O et al. *J Microbiol Biotechnol* 18:1773-1784, 2008; Daraths, K et al. *Journal of the American Chemical Society* 114:3956-3962, 1992; Li, K and Frost, J W. *Biotechnol Prog* 15:876-883, 1999; Lutke-Eversloh, T and Stephanopoulos, G. *Appl Microbiol Biotechnol* 75:103-110, 2007; Patnaik, R and Liao, J C. *Appl Environ Microbiol* 60:3903-3908, 1994; Yi, L et al. *Biotechnol Prog* 19:1450-1459, 2003; and Yi, J et al. *Biotechnol Prog* 18:1141-1148, 2002. In these previous studies, gene expression was modified for only a few candidates of the L-tyrosine pathway at a time, and a large number of strains had to be screened to circumvent bottlenecks. However, a problem with these approaches is that while one pathway bottleneck may be eliminated, a new bottleneck may be introduced somewhere else along the pathway.

Accordingly, there exists a need for improved approaches for engineering new microbial strains that contain all the genes necessary for producing amino acids and stable amino acid intermediates that reduces biosynthetic pathway bottlenecks and optimized the production of the amino acids and stable amino acids intermediates, thus improving overall product yield.

BRIEF SUMMARY

In order to meet the above needs, the present disclosure provides novel host cells containing recombinant polynucleotide containing shikimate biosynthesis pathway operons encoding the enzymes necessary for the production of shikimate from phosphoenolpyruvate and erythrose-4-phosphate and/or the enzymes necessary for the production of an aromatic amino acid from shikimate, where the operons increase the amount of shikimate and/or an aromatic amino acid produced by the cell, and the use of such host cells for increasing production of a tyrosine intermediate and an aromatic amino acid. Advantageously, the shikimate pathway operons of the present disclosure result in increased production of tyrosine intermediates and aromatic amino acids in a host cell.

Moreover, the present disclosure is based, at least in part, on the surprising discovery that microbial cells can be engineered to express a modular biosynthetic pathway for L-tyrosine production by encoding the enzymes for converting phosphoenolpyruvate (PEP) and erythrose-4-phosphate (E4P) to L-tyrosine on two plasmids. Advantageously, rational engineering to improve L-tyrosine production and to identify pathway bottlenecks was directed by targeted proteomics and metabolite profiling. The bottlenecks in the pathway were relieved by modification in plasmid copy number, promoter strength, gene codon usage, and the placement of genes in operons. One major bottleneck was found to be due to the bifunctional activities of the quinate/shikimate dehydrogenase (YdiB), which caused accumulation of intermediates dehydroquinate (DHQ) and dehydroshikimate (DHS), as well as the side product quinate. This bottleneck was relieved by replacing YdiB with its paralog AroE resulting in the production of over 700 mg/L of shikimate. Another bottleneck in shikimate production that was found to be due to low expression of the dehydroquinate synthase (AroB). This additional bottleneck was alleviated by optimizing the first 15 codons of the gene encoding AroB. Additionally, it was found that shikimate conversion to L-tyrosine was improved by replacing the shikimate kinase AroK with its isozyme AroL. Advantageously use of AroL effectively consumed all intermediates formed in the first half of the pathway. Moreover, guided by protein and metabolite measurements, the best engineered L-tyrosine producer, which contained two medium-copy, dual-operon plasmids, was optimized to produce over 2 g/L L-tyrosine at 80% of theoretical yield.

Accordingly, certain aspects of the present disclosure relate to a host cell containing a recombinant polynucleotide, where the recombinant polynucleotide contains an operon encoding the enzymes necessary for the production of shikimate from phosphoenolpyruvate and erythrose-4-phosphate, where the cell produces shikimate in an amount greater than that of a corresponding cell lacking the recombinant polynucleotide.

Other aspects of the present disclosure relate to a host cell containing a) shikimate, b) phosphoenolpyruvate, c) erythrose-4-phosphate, and d) a recombinant polynucleotide, where the recombinant polynucleotide contains an operon encoding the enzymes necessary for the production of the shikimate in the cell from the phosphoenolpyruvate and the erythrose-4-phosphate, where the shikimate produced in the cell is produced in an amount greater than that of a corresponding cell lacking the recombinant polynucleotide.

In certain embodiments that may be combined with any of the preceding embodiments, the operon encodes an AroE enzyme, an AroD enzyme, an AroB enzyme, an AroG enzyme, a PpsA enzyme, and a TktA enzyme. In certain embodiments, the genes encoding an AroE enzyme, an AroD enzyme, an AroB enzyme, an AroG enzyme, a PpsA enzyme, and a TktA enzyme are arranged in an order that is opposite to that of the shikimate biosynthesis mechanism. In certain embodiments that may be combined with any of the preceding embodiments, the operon encodes a YdiB enzyme, an AroD enzyme, an AroB enzyme, an AroG enzyme, a PpsA enzyme, and a TktA enzyme. In certain embodiments, the host cell further produces dehydroshikimate, dehydroquinate, and quinate in an amount greater than that of a corresponding cell lacking the recombinant polynucleotide. In certain embodiments, the genes encoding a YdiB enzyme, an AroD enzyme, an AroB enzyme, an AroG enzyme, a PpsA enzyme, and a TktA enzyme are arranged in an order that is opposite to that of the shikimate, dehydroshikimate, dehydroquinate, and quinate biosynthesis mechanism. In certain embodiments that may be combined with any of the preceding embodiments, the AroB enzyme is codon optimized. In certain embodiments that may be combined with any of the preceding embodiments, the AroG enzyme contains a point mutation. In certain embodiments, the point mutation is an Asp to Asn point mutation. In certain embodiments, the Asp to Asn point mutation is located at position 146 of the polypeptide sequence of the AroG enzyme. In certain embodiments that may be combined with any of the preceding embodiments, the operon is operably linked to a first regulatory sequence. In certain embodiments, the first regulatory sequence is an inducible promoter. In certain embodiments, the first regulatory sequence is a $P_{luc-UV5}$ promoter. In certain embodiments that may be combined with any of the preceding embodiments, the operon contains a second regulatory sequence located after the gene encoding the AroG enzyme. In certain embodiments, the second regulatory sequence is a constitutive promoter. In certain embodiments, the second regulatory sequence is a $P_{Ltet-O1}$ or a $T1-P_{TRC}$ terminator-promoter combination.

In certain embodiments that may be combined with any of the preceding embodiments, the host cell further contains a second recombinant polynucleotide, where the second recombinant polynucleotide contains a second operon encoding the enzymes necessary for the production of an aromatic amino acid from shikimate, where the cell produces the aromatic amino acid in an amount greater than that of a corresponding cell lacking the second recombinant polynucleotide. In certain embodiments, the aromatic amino acid is tyrosine. In certain embodiments, the second operon encodes a TyrB enzyme, a TyrA enzyme, an AroC enzyme, an AroA enzyme, and an AroL or AroK enzyme. In certain embodiments, the genes encoding a TyrB enzyme, a TyrA enzyme, an AroC enzyme, an AroA enzyme, and an AroL or AroK enzyme are arranged in an order that is opposite to that of the tyrosine biosynthesis mechanism. In certain embodiments that may be combined with any of the preceding embodiments, where the TyrA enzyme contains at least one point mutation. In certain embodiments, the at least one point mutation is a Met to Ile point mutation. In certain embodiments, the at least one point mutation is an Ala to Val point mutation. In certain embodiments, the TyrA enzyme contains two point mutations. In certain embodiments, the TyrA enzyme contains a Met to Ile point mutation at position 53 of the polypeptide sequence of the TyrA enzyme, and an Ala to Val point mutation at position 354 of the polypeptide sequence of the TyrA enzyme. In certain embodiments, the aromatic amino acid is tryptophan. In certain embodiments, the second operon encodes a TrpB or TrpA enzyme, a TrpC enzyme, a TrpD enzyme, a TrpE enzyme, an AroC enzyme, an AroA enzyme, and an AroL or AroK enzyme. In certain embodiments, the genes encoding a TrpB or TrpA enzyme, a TrpC enzyme, a TrpD enzyme, a TrpE enzyme, an AroC enzyme, an AroA enzyme, and an AroL or AroK enzyme are arranged in an order that is opposite to that of the tryptophan biosynthesis mechanism. In certain embodiments, the aromatic amino acid is phenylalanine. In certain embodiments, the second operon encodes a TyrB enzyme, a PheA enzyme, an AroC enzyme, an AroA enzyme, and an AroL or AroK enzyme. In certain embodiments, the genes encoding a TyrB enzyme, a PheA enzyme, an AroC enzyme, an AroA enzyme, and an AroL or AroK enzyme are arranged in an order that is opposite to that of the phenylalanine biosynthesis mechanism. In certain embodiment that may be combined with any of the preceding embodiments, the second operon is operably linked to a first regulatory sequence. In certain embodiments, the first regulatory sequence is an inducible promoter. In certain embodiments, the first regulatory sequence is a $P_{luc-UV5}$ promoter. In certain embodiments that may be combined with any of the preceding embodiments, the second operon further contains a second regulatory sequence located after the gene encoding the AroC enzyme. In certain embodiments, the second regulatory sequence is a continuative promoter. In certain embodiments, the second regulatory sequence is a T1-$P_{TRC}$ terminator-promoter combination or a $P_{Ltet-O1}$ promoter.

Other aspects of the present disclosure relate to a host cell containing a recombinant polynucleotide, where the recombinant polynucleotide contains an operon encoding the enzymes necessary for the production of an aromatic amino acid from shikimate, where the cell produces the aromatic amino acid in an amount greater than that of a corresponding cell lacking the recombinant polynucleotide.

Other aspects of the present disclosure relate to a host cell containing a) an aromatic amino acid, b) shikimate, and c) a recombinant polynucleotide, where the recombinant polynucleotide contains an operon encoding the enzymes necessary for the production of the aromatic amino acid in the cell from shikimate, where the aromatic amino acid produced in the cell is produced in an amount greater than that of a corresponding cell lacking the recombinant polynucleotide.

In certain embodiments that may be combined with any of the preceding embodiments, the aromatic amino acid is tyrosine. In certain embodiments, the operon encodes a TyrB enzyme, a TyrA enzyme, an AroC enzyme, an AroA enzyme, and an AroL or AroK enzyme. In certain embodiments, the genes encoding a TyrB enzyme, a TyrA enzyme, an AroC enzyme, an AroA enzyme, and an AroL or AroK enzyme are arranged in an order that is opposite to that of the tyrosine biosynthesis mechanism. In certain embodiments that may be combined with any of the preceding embodiments, the TyrA enzyme contains at least one point mutation. In certain embodiments, the at least one point mutation is a Met to Ile point mutation. In certain embodiments, the at least one point mutation is an Ala to Val point mutation. In certain embodiments, the TyrA enzyme contains two point mutations. In certain embodiments, the TyrA enzyme contains a Met to Ile point mutation at position 53 of the polypeptide sequence of the TyrA enzyme, and an Ala to Val point mutation at position 354 of the polypeptide sequence of the TyrA enzyme. In certain embodiments that may be combined with any of the preceding embodiments, the aromatic amino acid is tryptophan. In certain embodiments, the operon encodes a TrpB or TrpA enzyme, a TrpC enzyme, a TrpD enzyme, a TrpE enzyme, an AroC enzyme, an AroA enzyme, and an AroL or AroK enzyme. In certain embodiments, the genes encoding a TrpB or TrpA enzyme, a TrpC enzyme, a TrpD enzyme, a TrpE enzyme, an AroC enzyme, an AroA enzyme, and an AroL or AroK enzyme are arranged in an order that is opposite to that of the tryptophan biosynthesis mechanism. In certain embodiments that may be combined with any of the preceding embodiments, the aromatic amino acid is phenylalanine. In certain embodiments, the operon encodes a TyrB enzyme, a PheA enzyme, an AroC enzyme, an AroA enzyme, and an AroL or AroK enzyme. In certain embodiments, the genes encoding a TyrB enzyme, a PheA enzyme, an AroC enzyme, an AroA enzyme, and an AroL or AroK enzyme are arranged in an order that is opposite to that of the phenylalanine biosynthesis mechanism. In certain embodiments that may be combined with any of the preceding embodiments, the operon is operably linked to a first regulatory sequence. In certain embodiments, the first regulatory sequence is an inducible promoter. In certain embodiments, the first regulatory sequence is a $P_{luc-UV5}$ promoter. In certain embodiments that may be combined with any of the preceding embodiments, the operon further contains a second regulatory sequence located after the gene encoding the AroC enzyme. In certain embodiments, the second regulatory sequence is a continuative promoter. In certain embodiments, the second regulatory sequence is a T1-$P_{TRC}$ terminator-promoter combination or a $P_{Ltet-O1}$ promoter. In certain embodiments that may be combined with any of the preceding embodiments, the host cell further contains a second a recombinant polynucleotide, where the second recombinant polynucleotide contains a second operon encoding the enzymes necessary for the production of shikimate from phosphoenolpyruvate and erythrose-4-phosphate, where the cell produces shikimate in an amount greater than that of a corresponding cell lacking the second recombinant polynucleotide.

Other aspects of the present disclosure relate to a host cell containing: a first recombinant polynucleotide, where the first recombinant polynucleotide contains a first operon encoding the enzymes necessary for the production of shikimate from phosphoenolpyruvate and erythrose-4-phosphate; and a second recombinant polynucleotide, where the recombinant polynucleotide contains a second operon encoding the enzymes necessary for the production of an aromatic amino acid from shikimate, where the cell produces shikimate in an amount greater than that of a corresponding cell lacking the first recombinant polynucleotide and where the cell produces the aromatic amino acid in an amount greater than that of a corresponding cell lacking the second recombinant polynucleotide.

Other aspects of the present disclosure relate to a host cell containing a) an aromatic amino acid, b) shikimate, c) phosphoenolpyruvate, d) erythrose-4-phosphate, e) a first recombinant polynucleotide, where the recombinant polynucleotide contains an operon encoding the enzymes necessary for the production of the shikimate in the cell from the phosphoenolpyruvate and the erythrose-4-phosphate, and f) a second recombinant polynucleotide, where the recombinant polynucleotide contains an operon encoding the enzymes necessary for the production of the aromatic amino acid in the cell from shikimate, where the shikimate produced in the cell is produced in an amount greater than that of a corresponding cell lacking the first recombinant polynucleotide, and where the aromatic amino acid produced in the cell is produced in an amount greater than that of a corresponding cell lacking the second recombinant polynucleotide.

In certain embodiments that may be combined with any of the preceding embodiments, the first operon encodes an AroE enzyme, an AroD enzyme, an AroB enzyme, an AroG enzyme, a PpsA enzyme, and a TktA enzyme. In certain embodiments, the genes encoding an AroE enzyme, an AroD enzyme, an AroB enzyme, an AroG enzyme, a PpsA enzyme, and a TktA enzyme are arranged in an order that is opposite to that of the shikimate biosynthesis mechanism. In certain embodiments that may be combined with any of the preceding embodiments, the AroB enzyme is codon optimized. In certain embodiments that may be combined with any of the preceding embodiments, the AroG enzyme contains a point mutation. In certain embodiments, the point mutation is an Asp to Asn point mutation. In certain embodiments, the Asp to Asn point mutation is located at position 146 of the polypeptide sequence of the AroG enzyme. In certain embodiments that may be combined with any of the preceding embodiments, the first operon is operably linked to a first regulatory sequence. In certain embodiments, the first regulatory sequence is an inducible promoter. In certain embodiments, the first regulatory sequence is a $P_{luc-UV5}$ promoter. In certain embodiments that may be combined with any of the preceding embodiments, the first operon contains a second regulatory sequence located after the gene encoding the AroG enzyme. In certain embodiments, the second regulatory sequence is a constitutive promoter. In certain embodiments, the second regulatory sequence is a $P_{Ltet-O1}$ or a T1-$P_{TRC}$ terminator-promoter combination. In certain embodiments that may be combined with any of the preceding embodiments, the aromatic amino acid is tyrosine. In certain embodiments, the second operon encodes a TyrB enzyme, a TyrA enzyme, an AroC enzyme, an AroA enzyme, and an AroL or AroK enzyme. In certain embodiments, the genes encoding a TyrB enzyme, a TyrA enzyme, an AroC enzyme, an AroA enzyme, and an AroL or AroK enzyme are arranged in an order that is opposite to that of the tyrosine biosynthesis mechanism. In certain embodiments that may be combined with any of the preceding embodiments, the TyrA enzyme contains at least one point mutation. In certain embodiments, the at least one point mutation is a Met to Ile point mutation. In certain embodiments, the at least one point mutation is an Ala to Val point mutation. In certain embodiments, the TyrA enzyme contains two point mutations. In certain embodiments, the TyrA enzyme contains a Met to Ile point mutation at position 53 of the polypeptide sequence of the TyrA enzyme, and an Ala to Val point mutation at position 354 of the polypeptide sequence of the TyrA enzyme. In certain embodiments that may be combined with any of the preceding embodiments, the aromatic amino acid is tryptophan. In certain embodiments, the second operon encodes a TrpB or TrpA enzyme, a TrpC enzyme, a TrpD enzyme, a TrpE enzyme, an AroC enzyme, an AroA enzyme, and an AroL or AroK enzyme. In certain embodiments, the genes encoding a TrpB or TrpA enzyme, a TrpC enzyme, a TrpD enzyme, a TrpE enzyme, an AroC enzyme, an AroA enzyme, and an AroL or AroK enzyme are arranged in an order that is opposite to that of the tryptophan biosynthesis mechanism. In certain embodiments that may be combined with any of the preceding embodiments, the aromatic amino acid is phenylalanine. In certain embodiments, the second operon encodes a TyrB enzyme, a PheA enzyme, an AroC enzyme, an AroA enzyme, and an AroL or AroK enzyme. In certain embodiments, the genes encoding a TyrB enzyme, a PheA enzyme, an AroC enzyme, an AroA enzyme, and an AroL or AroK enzyme are arranged in an order that is opposite to that of the phenylalanine biosynthesis mechanism. In certain embodiments that may be combined with any of the preceding embodiments, the second operon is operably linked to a first regulatory sequence. In certain embodiments, the first regulatory sequence is an inducible promoter. In certain embodiments, the first regulatory sequence is a $P_{luc-UV5}$ promoter. In certain embodiments that may be combined with any of the preceding embodiments, the second operon contains a second regulatory sequence located after the gene encoding the AroC enzyme. In certain embodiments, the second regulatory sequence is a continuative promoter. In certain embodiments, the second regulatory sequence is a T1-$P_{TRC}$ terminator-promoter combination or a $P_{Ltet-O1}$ promoter.

In certain embodiments that may be combined with any of the preceding embodiments, the recombinant polynucleotide, the first recombinant polynucleotide, and/or the second recombinant polynucleotide are incorporated into the genome of the host cell. In certain embodiments that may be combined with any of the preceding embodiments, the host cell further contains the proteins necessary to produce a commodity chemical. In certain embodiments that may be combined with any of the preceding embodiments, the host cell is a microorganism. In certain embodiments that may be combined with any of the preceding embodiments, the host cell is *E. coli*.

Other aspects of the present disclosure relate to a method of increasing production of a tyrosine intermediate in a host cell, by: a) providing the host cell of any of the preceding embodiments; and b) culturing the cell in a medium such that the recombinant polynucleotide is expressed, where expression of the recombinant polynucleotide results in increased production of a tyrosine intermediate compared to a corresponding cell lacking the recombinant polynucleotide.

In certain embodiments, the tyrosine intermediate is selected from shikimate, dehydroshikimate, dehydroquinate, and quinate. In certain embodiments, the tyrosine intermediate is shikimate. In certain embodiments, the host cell produces from about 50 mg/L to about 1,000 mg/L of shikimate. In certain embodiments, the host cell produces from about 80 mg/L to about 760 mg/L of shikimate. In certain embodiments, the host cell produces f from about 79 mg/L to about 759 mg/L of shikimate. In certain embodiments, the host cell produces at least about 50 mg/L, at least about 60 mg/L, at least about 70 mg/L, at least about 79 mg/L, at least about 80 mg/L, at least about 90 mg/L, at least about 100 mg/L, at least about 150 mg/L, at least about 194 mg/L, at least about 200 mg/L, at least about 250 mg/L, at least about 273 mg/L, at least about 278 mg/L, at least about 300 mg/L, at least about 350 mg/L, at least about 400 mg/L, at least about 450 mg/L, at least about 500 mg/L, at least about 510 mg/L, at least about 550 mg/L, at least about 600 mg/L, at least about 650 mg/L, at least about 700 mg/L, at least about 750 mg/L, at least about 759 mg/L, at least about 800 mg/L, at least about 850 mg/L, at least about 900 mg/L, at least about 950 mg/L, or at least about 1,000 mg/L of shikimate. In certain embodiments, the host cell produces from about 50 mg/L to about 1,500 mg/L of dehydroshikimate. In certain embodiments, the host cell produces from about 45 mg/L to about 1,230 mg/L of dehydroshikimate. In certain embodiments, the host cell produces from about 1 mg/L to about 100 mg/L of dehydroquinate. In certain embodiments, the host cell produces from about 3 mg/L to about 60 mg/L of dehydroquinate. In certain embodiments, the host cell produces from about 1 mg/L to about 250 mg/L of quinate. In certain embodiments, the host cell produces from about 2 mg/L to about 245 mg/L of quinate. In certain embodiments that may be combined with any of the preceding embodiments, the recombinant polynucleotide is incorporated into the genome of the host cell.

Other aspects of the present disclosure relate to a method of increasing production of an aromatic amino acid in a host cell, by: a) providing a host cell of any of the preceding embodiments containing a first recombinant polynucleotide that contains an operon encoding the enzymes necessary for the production of shikimate from phosphoenolpyruvate and erythrose-4-phosphate and a second recombinant polynucleotide that contains an operon encoding the enzymes necessary for the production of an aromatic amino acid from shikimate; and b) culturing the cell in a medium such that the first and second recombinant polynucleotides are expressed, where expression of the first and second recombinant polynucleotides results in increased production of an aromatic amino acid compared to a corresponding cell lacking the first and second recombinant polynucleotides.

In certain embodiments, the aromatic amino acid is selected from tyrosine, tryptophan, and phenylalanine. In certain embodiments, the aromatic amino acid is tyrosine. In certain embodiments, the host cell produces from about 0.75 g/L to about 2.7 g/L of tyrosine. In certain embodiments, the host cell produces from about 0.75 g/L to about 2.17 g/L of tyrosine. In certain embodiments, the host cell produces at least about 0.746 g/L, at least about 0.75 g/L, at least about 0.8 g/L, at least about 0.897 g/L, at least about 0.9 g/L, at least about 0.908 g/L, at least about 1 g/L, at least about 1.15 g/L, at least about 1.22 g/L, at least about 1.25 g/L, at least about 1.31 g/L, at least about 1.5 g/L, at least, at least about 1.75 g/L, at least about 2 g/L, at least about 2.1 g/L, at least about 2.17 g/L, at least about 2.2 g/L, at least about 2.3 g/L, at least about 2.4 g/L, at least about 2.5 g/L, at least about 2.6 g/L, or at least about 2.7 g/L of tyrosine. In certain embodiments, the host cell produces a tyrosine yield that is from about 5% to about 220% greater than an amount of tyrosine produce by the corresponding cell lacking the first and second recombinant polynucleotides. In certain embodiments, the host cell produces a tyrosine yield that is from about 6.5% to about 210% greater than an amount of tyrosine produce by the corresponding cell lacking the first and second recombinant polynucleotides. In certain embodiments, the host cell produces a tyrosine yield that is at least about 5%, at least about 6%, at least about 6.5%, at least about 7%, at least about 8%, at least about 10%, at least about 15%, at least about 20%, at least about 25%, at least about 26%, at least about 27%, at least about 28%, at least about 30%, at least about 35%, at least about 40%, at least about 45%, at least about 50%, at least about 55%, at least about 60%, at least about 61%, at least about 62%, at least about 63%, at least about 64%, at least about 65%, at least about 70%, at least about 71%, at least about 72%, at least about 73%, at least about 74%, at least about 75%, at least about 80%, at least about 85%, at least about 86%, at least about 87%, at least about 88%, at least about 89%, at least about 90%, at least about 95%, at least about 100%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, at least about 200%, at least about 205%, at least about 206%, at least about 207%, at least about 208%, at least about 210%, at least about 211%, at least about 212%, at least about 214%, at least about 215%, or at least about 220% greater than an amount of tyrosine produce by the corresponding cell lacking the first and second recombinant polynucleotides. In certain embodiments, the tyrosine is produced at a percentage yield that is from about 27% to about 95% of the theoretical maximal yield. In certain embodiments, the tyrosine is produced at a percentage yield that is from about 27% to about 79% of the theoretical maximal yield. In certain embodiments, the tyrosine is produced at a percentage yield that is at least about 27%, at least about 33%, at least about 40%, at least about 42%, at least about 44%, at least about 60%, at least about 65%, at least about 70%, at least about 75%, at least about 79%, at least about 80%, at least about 90%, or at least about 95% of the theoretical maximal yield. In certain embodiments, the tyrosine is produced at a percentage of the theoretical maximal yield that is from about 5% to about 220% greater than the percentage of the theoretical maximal yield of tyrosine produced by the corresponding cell lacking the first and second recombinant polynucleotides. In certain embodiments, the tyrosine is produced at a percentage of the theoretical maximal yield that is from about 8% to about 216% greater than the percentage of the theoretical maximal yield of tyrosine produced by the corresponding cell lacking the first and second recombinant polynucleotides. In certain embodiments, the tyrosine is produced at a percentage of the theoretical maximal yield that is at least about 5%, at least about 6%, at least about 7%, at least about 8%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 40%, at least about 45%, at least about 50%, at least about 55%, at least about 60%, at least about 65%, at least about 66%, at least about 67%, at least about 68%, at least about 69%, at least about 70%, at least about 75%, at least about 76%, at least about 77%, at least about 78%, at least about 79%, at least about 80%, at least about 85%, at least about 90%, at least about 91%, at least about 92%, at least about 93%, at least about 94%, at least about 95%, at least about 100%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, at least about 200%, at least about 205%, at least about 210%, at least about 211%, at least about 212%, at least about 213%, at least about 214%, at least about 215%, at least about 216%, at least about 217%, at least about 218%, at least about 219%, or at least about 220% greater than the percentage of the theoretical maximal yield of tyrosine produced by the corresponding cell lacking the first and second recombinant polynucleotides.

In certain embodiments that may be combined with any of the preceding embodiments, the host cell further contains the proteins necessary to produce a commodity chemical. In certain embodiments that may be combined with any of the preceding embodiments, the host cell is a microorganism. In certain embodiments that may be combined with any of the preceding embodiments, the host cell is E. coli.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION

Definitions

Figure 1:
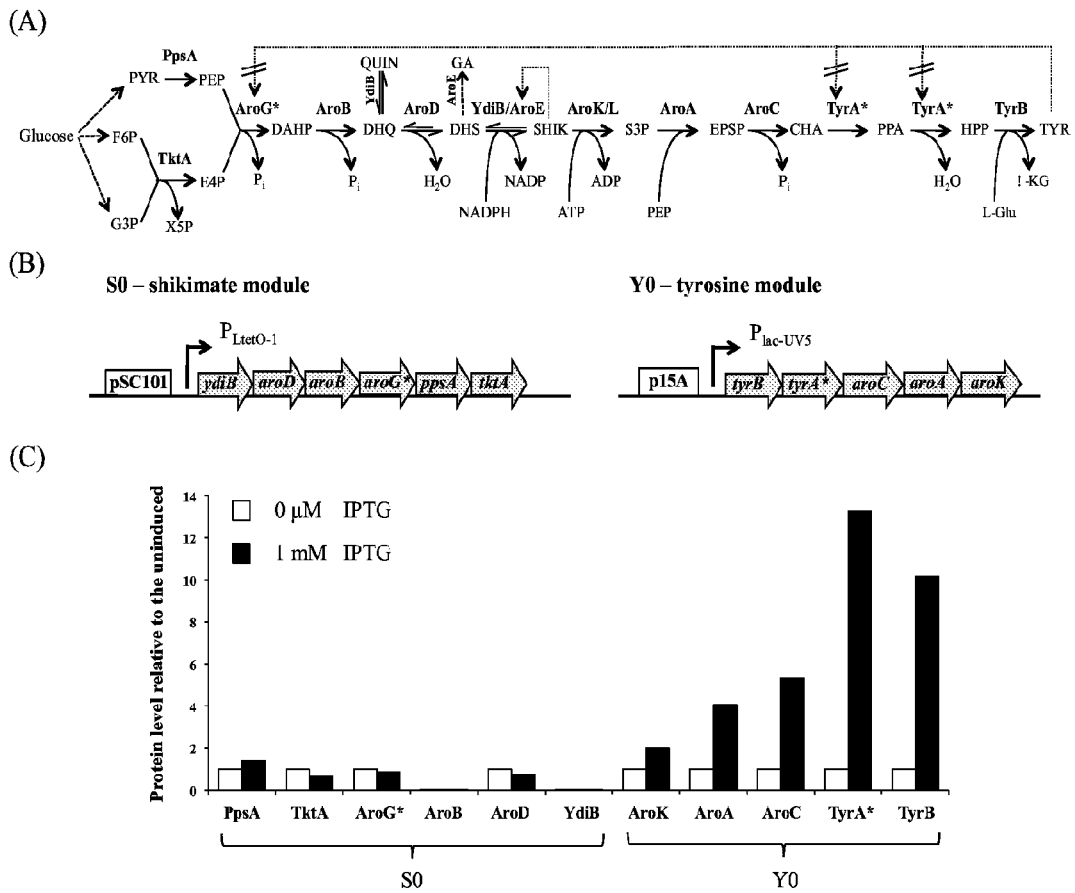
FIG. 1A depicts the biosynthetic pathway of L-tyrosine (TYR) in E. coli from glucose. X5P corresponds to xylulose 5-phosphate; F6P corresponds to fructose 6-phosphate; PYR corresponds to pyruvate; PEP corresponds to phosphoenolpyruvate; E4P corresponds to erythrose 4-phosphate; G3P corresponds to glyceraldehyde 3-phosphate; DAHP corresponds to 3-deoxy-D-arobino-heptulosonate 7-phosphate; DHQ corresponds to 3-dehydroquinate; DHS corresponds to 3-dehydroshikimate; SHIK corresponds to shikimate; S3P corresponds to shikimate 3-phosphate; EPSP corresponds to 5-enolpyruvoylshikimate 3-phosphate; CHA corresponds to chorismate; PPA corresponds to prephenate; HPP corresponds to 4-hydroxyphenlypyruvate; L-Glu, glutamic acid; and α-KG, α-ketoglutarate. The enzymes (in bold) are PpsA, phosphoenolpyruvate synthase; TktA corresponds to transketolase A; AroG corresponds to DAHP synthase; AroB corresponds to DHQ synthase; AroD corresponds to DHQ dehydratase; YdiB corresponds to quinate/shikimate dehydrogenase; AroE corresponds to shikimate dehydrogenase; AroK/L corresponds to shikimate kinase I/II; AroA corresponds to EPSP synthase; AroC corresponds to chorismate synthase; TyrA corresponds to the chorismate mutase/prephenate dehydrogenase bifunctional enzyme; and TyrB corresponds to aromatic amino acid aminotransferase. QUIN and GA are side products quinate and gallic acid, respectively. QUIN is formed by YdiB from DHQ (18), while GA formed by AroE from DHS (18, 30). Dashed lines indicate where feedback inhibitions occur. Allosteric regulation of AroG and TyrA were removed by employing their respective feedback resistant mutants, AroG*[D146N] and TyrA*[M53I;A354V], respectively.
FIG. 1B depicts the structure of the initial modules, S0 and Y0, for production of shikimate and L-tyrosine, respectively. Open blocks indicate the origin of replication; shaded block arrows indicate the genes; and the angled arrows indicate the promoters. For each operon, the genes are placed in the reverse order relative to the reaction pathway.
FIG. 1C depicts SRM analysis of the protein production levels from S0 and Y0 in Strain A, when induced or uninduced with IPTG.

Unless defined otherwise, all scientific and technical terms are understood to have the same meaning as commonly used in the art to which they pertain. For the purpose of the present disclosure, the following terms are defined.

As used herein, "operon" refers to a configuration of separate genes that are transcribed in tandem as a single messenger RNA. For example, the genes encoding the enzymes necessary for a host cell to synthesize shikimate from phosphoenolpyruvate (PEP) and erythrose-4-phosphate (E4P) may be configured together so that they are transcribed together as a single messenger RNA. An "operon" of the present disclosure may include a group of two or more genes under the control of a single regulatory sequence, such as a promoter. Additionally, the transcribed genes of an "operon" of the present disclosure may be either translated together or each gene may be translated separately.

As used herein, "arranged in an order that is opposite to that of the shikimate biosynthesis mechanism" refers to arranging the genes encoding the enzymes necessary for the production of shikimate on an operon such that the genes are placed in the reverse order relative to the biosynthesis pathway. For example, aroE, which catalyzes the last step in the formation of shikimate is placed next to the promoter, aroD, which catalyzes the second to last step in the formation of shikimate, is placed next to the aroE gene, etc.

As used herein, "arranged in an order that is opposite to that of the shikimate, dehydroshikimate, dehydroquinate, and quinate biosynthesis mechanism" refers to arranging the genes encoding the enzymes necessary for the production of shikimate, dehydroshikimate, dehydroquinate, and quinate on an operon such that the genes are placed in the reverse order relative to the biosynthesis pathway. For example, ydiB, which catalyzes the last step in the formation of shikimate, dehydroshikimate, dehydroquinate, and quinate is placed next to the promoter; aroD, which catalyzes the second to last step in the pathway, is placed next to the ydiB gene, etc.

As used herein, "arranged in an order that is opposite to that of the tyrosine biosynthesis mechanism" refers to arranging the genes encoding the enzymes necessary for the production of tyrosine on an operon such that the genes are placed in the reverse order relative to the biosynthesis pathway. For example, tyrB, which catalyzes the last step in the formation of tyrosine is placed next to the promoter, tyrA, which catalyzes the second to last step in the pathway, is placed next to the tyrB gene, etc.

As used herein, "arranged in an order that is opposite to that of the tryptophan biosynthesis mechanism" refers to arranging the genes encoding the enzymes necessary for the production of tryptophan on an operon such that the genes are placed in the reverse order relative to the biosynthesis pathway. For example, trprB, which catalyzes the last step in the formation of tryptophan is placed next to the promoter, trpA, which catalyzes the second to last step in the pathway, is placed next to the trpB gene, etc.

As used herein, "arranged in an order that is opposite to that of the phenylalanine biosynthesis mechanism" refers to arranging the genes encoding the enzymes necessary for the production of phenylalanine on an operon such that the genes are placed in the reverse order relative to the biosynthesis pathway. For example, tyrB, which catalyzes the last step in the formation of phenylalanine is placed next to the promoter, pheA, which catalyzes the second to last step in the pathway, is placed next to the tyrB gene, etc.

Overview

The present disclosure is based on the surprising discovery that microorganisms, such as *E. coli*, engineered to express a recombinant bi-modular L-tyrosine biosynthetic pathway produce L-tyrosine in an amount that is at least 80% of the theoretical yield. Advantageously, each module can be individually expressed in the microorganisms to produce an increased amount of shikimate from phosphoenolpyruvate (PEP) and erythrose-4-phosphate (E4P), or L-tyrosine from shikimate, respectively.

Accordingly, certain aspects of the present disclosure provide host cells containing a recombinant polynucleotide, where the recombinant polynucleotide contains an operon encoding the enzymes necessary for the production of shikimate and/or a shikimate derivative from phosphoenolpyruvate and erythrose-4-phosphate, where the cell produces shikimate in an amount greater than that of a corresponding cell lacking the recombinant polynucleotide.

Other aspects of the present disclosure provide host cells containing a recombinant polynucleotide, where the recombinant polynucleotide contains an operon encoding the enzymes necessary for the production of an aromatic amino acid from shikimate and/or a shikimate derivative, where the cell produces the aromatic amino acid in an amount greater than that of a corresponding cell lacking the recombinant polynucleotide.

Further aspects of the present disclosure provide host cells containing: a first recombinant polynucleotide, where the first recombinant polynucleotide contains a first operon encoding the enzymes necessary for the production of shikimate from phosphoenolpyruvate and erythrose-4-phosphate; and a second recombinant polynucleotide, where the recombinant polynucleotide contains a second operon encoding the enzymes necessary for the production of an aromatic amino acid from shikimate, where the cell produces shikimate in an amount greater than that of a corresponding cell lacking the first recombinant polynucleotide and where the cell produces the aromatic amino acid in an amount greater than that of a corresponding cell lacking the second recombinant polynucleotide.

Other aspects of the present disclosure provide methods of increasing production of a tyrosine intermediate in a host cell, by: a) providing a host cell of the present disclosure containing a recombinant polynucleotide containing an operon encoding the enzymes necessary for the production of shikimate and/or a shikimate derivative from phosphoenolpyruvate and erythrose-4-phosphateany of the preceding embodiments; and b) culturing the cell in a medium such that the recombinant polynucleotide is expressed, where expression of the recombinant polynucleotide results in increased production of a tyrosine intermediate compared to a corresponding cell lacking the recombinant polynucleotide.

Further aspects of the present disclosure provide methods of increasing production of an aromatic amino acid in a host cell, by: a) providing a host cell of the present disclosure containing a first recombinant polynucleotide containing an operon encoding the enzymes necessary for the production of shikimate from phosphoenolpyruvate and erythrose-4-phosphate; and a second recombinant polynucleotide containing an operon encoding the enzymes necessary for the production of an aromatic amino acid from shikimate; and b) culturing the cell in a medium such that the first and second recombinant polynucleotides are expressed, where expression of the first and second recombinant polynucleotides results in increased production of an aromatic amino acid compared to a corresponding cell lacking the first and second recombinant polynucleotides.

Host Cells

Certain aspects of the present disclosure relate to host cells containing a recombinant polynucleotide containing an operon encoding the enzymes necessary for the production of shikimate and/or a shikimate intermediate from phosphoenolpyruvate and erythrose-4-phosphate, and/or a recombinant polynucleotide containing an operon encoding the enzymes necessary for the production of an aromatic amino acid from shikimate and/or shikimate intermediate.

"Host cell" and "host microorganism" are used interchangeably herein to refer to a living biological cell that can be transformed via insertion of recombinant DNA or RNA. Such recombinant DNA or RNA can be in an expression vector. Thus, a host cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

Any suitable prokaryotic or eukaryotic host cell may be used in the present disclosure so long as it remains viable after being transformed with a recombinant polynucleotide. In certain preferred embodiments, the host cell is a bacterial cell. Examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, and *Paracoccus taxonomical* classes. Preferably, the host cell is not adversely affected by the transduction of the necessary recombinant polynucleotide sequences, the subsequent expression of the proteins (e.g., enzymes), or the resulting intermediates. More preferably, the bacterial host cell is an *Escherichia coli* (*E. coli*) cell.

Suitable eukaryotic host cells include, without limitation, fungal cells, plant cells, insect cells, and mammalian cells. Suitable fungal cells are yeast cells, such as yeast cells of the *Saccharomyces* genus.

The host cells of the present disclosure are genetically modified in that recombinant polynucleotides have been introduced into the host cells, and as such the genetically modified host cells do not occur in nature. A suitable host cell of the present disclosure is one capable of expressing one or more polynucleotide constructs encoding enzymes involved in a desired biosynthetic pathway, such as a shikimate and/or aromatic amino acid biosynthetic pathway.

As used herein, the terms "polynucleotide," "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; inter-nucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochem. 9:4022, 1970).

A "recombinant polynucleotide" or "heterologous polynucleotide" refers to a polymer of nucleic acids wherein at least one of the following is true: (a) the sequence of nucleic acids is foreign to (i.e., not naturally found in) a given host cell; (b) the sequence may be naturally found in a given host cell, but is present in an unnatural (e.g., greater than expected) amount; or (c) the sequence of polynucleotides comprises two or more subsequences that are not found in the same relationship to each other in nature. For example, regarding instance (c), a recombinant polynucleotide sequence will have two or more sequences from unrelated genes arranged to make a new functional polynucleotide. Specifically, the present disclosure describes the introduction of an expression vector into a host cell, wherein the expression vector contains a polynucleotide sequence coding for an operon containing two or more genes each encoding an enzyme that is not normally found in a host cell or encoding an enzyme that is normally found in the cell but is under the control of one or more different regulatory sequences. With reference to the host cell's genome, then, the polynucleotide sequence that codes for the two or more enzymes is recombinant.

As used herein, a "polypeptide" is an amino acid sequence containing a plurality of consecutive polymerized amino acid residues (e.g., at least about 15 consecutive polymerized amino acid residues, at least about 30 consecutive polymerized amino acid residues, at least about 50 consecutive polymerized amino acid residues, or more consecutive polymerized amino acid residues). In many instances, a polypeptide contains a polymerized amino acid residue sequence that is an enzyme, or a domain or portion or fragment thereof. An enzyme can catalyze a chemical reaction, such as the reduction of shikimate to 3-dehydroshikimate in a host cell. The polypeptide optionally contains modified amino acid residues, naturally occurring amino acid residues not encoded by a codon, and non-naturally occurring amino acid residues. A "protein" of the present disclosure refers to an amino acid sequence, oligopeptide, peptide, polypeptide, or portions thereof whether naturally occurring or synthetic.

Genes and proteins that may be used in the present disclosure include genes encoding conservatively modified variants and proteins that are conservatively modified variants of those genes and proteins described throughout the disclosure. "Conservatively modified variants" as used herein include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Homologs of the genes and proteins described herein may also be used in the present disclosure. As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

As used herein, "orthologs" are evolutionarily related genes or proteins in different species that have similar sequences and functions, and that develop through a speciation event. Sequences that are orthologs are referred to as being "orthologous" to each other. As used herein, "paralogs" are evolutionarily related genes or proteins in the same organism that have similar sequences and functions, and that develop through a gene duplication event. Sequences that are paralogs are referred to as being "paralogous" to each other.

The terms "identical" or percent "identity," in the context of two or more polynucleotide or polypeptide sequences, refer to two or more sequences or subsequences that are the same. Two sequences are "substantially identical" if the two sequences have a specified percentage of amino acid residues or nucleotides that are the same (i.e., 30%, 35%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8): 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for polynucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for polynucleotide sequences) uses as defaults a wordlength (W) of 11, an expectation (E) or 10, M=5, N=−4, and a comparison of both strands. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877). One measure of similarity provided by the BLAST algorithm is the smallest sum probability (P(N)), which provides an indication of the probability by which a match between two polynucleotide or amino acid sequences would occur by chance. For example, a polynucleotide is considered similar to a reference sequence if the smallest sum probability in a comparison of the test polynucleotide to the reference polynucleotide is less than about 0.2, more preferably less than about 0.01, and most preferably less than about 0.001.

Other than percentage of sequence identity noted above, another indication that two polynucleotide sequences or polypeptides are substantially identical is that the polypeptide encoded by the first polynucleotide is immunologically cross-reactive with the antibodies raised against the polypeptide encoded by the second polynucleotide. Thus, a polypeptide is typically substantially identical to a second polypeptide, for example, where the two peptides differ only by conservative substitutions. Another indication that two polynucleotide sequences are substantially identical is that the two molecules or their complements hybridize to each other under stringent conditions. Yet another indication that two polynucleotide sequences are substantially identical is that the same primers can be used to amplify the sequence.

"Genetically engineered" or "genetically modified" refers to any host cell modified by any recombinant DNA or RNA technology. In other words, the host cell has been transfected, transformed, or transduced with a recombinant polynucleotide molecule, and thereby been altered so as to cause the host cell to alter expression of a desired protein. Methods and vectors for genetically engineering host cells are well known in the art; for example, various techniques are illustrated in *Current Protocols in Molecular Biology*, Ausubel et al., eds. (Wiley & Sons, New York, 1988, and quarterly updates).

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification in the host cell in question that results in increased expression and/or functionality (biological activity) of the enzymes or proteins and includes higher activity of the enzymes (e.g., specific activity or in vivo enzymatic activity), reduced inhibition or degradation of the enzymes, and overexpression of the enzymes. For example, gene copy number can be increased, expression levels can be increased by use of a promoter that gives higher levels of expression than that of the native promoter, or a gene can be altered by genetic engineering or classical mutagenesis to increase the biological activity of an enzyme. Combinations of some of these modifications are also possible.

In general, according to the present disclosure, an increase or a decrease in a given characteristic of a mutant or modified enzyme (e.g., enzyme activity) is made with reference to the same characteristic of a wild-type (i.e., normal, not modified) enzyme that is derived from the same organism (i.e., from the same source or parent sequence), and is measured or established under the same or equivalent conditions. Similarly, an increase or decrease in a characteristic of a genetically modified host microorganism (e.g., expression and/or biological activity of a protein, or production of a product) is made with reference to the same characteristic of a wild-type microorganism of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the host microorganism is measured, as well as the type of assay used, the host microorganism that is evaluated, etc. As discussed above, equivalent conditions are conditions (e.g., culture conditions) which are similar, but not necessarily identical (e.g., some conservative changes in conditions can be tolerated), and which do not substantially change the effect on microbe growth or enzyme expression or biological activity as compared to a comparison made under the same conditions.

Preferably, a genetically modified host microorganism that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are preferred when comparing the activity of an isolated modified polynucleotide molecule or protein directly to the activity of an isolated wild-type polynucleotide molecule or protein (e.g., if the comparison is done in vitro as compared to in vivo).

In another aspect of the present disclosure, a genetically modified host microorganism that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

Accordingly, in some embodiments, a host cell of the present disclosure contains and expresses one or more recombinant operons encoding one or more enzymes including, without limitation, an AroA enzyme, an AroB enzyme, an AroC enzyme, an AroD enzyme, an AroE enzyme, an AroG enzyme, an AroL or AroK enzyme, a YdiB enzyme, a PpsA enzyme, a TktA enzyme, a TyrA enzyme, a TyrB enzyme, a TrpA enzyme, a TrpB enzyme, a TrpC enzyme, a TrpD enzyme, a TrpE enzyme, and an a PheA enzyme Preferably, the encoded enzymes catalyze reactions that lead to the production of shikimate, a shikimate intermediate, and/or an aromatic amino acid, such as tyrosine, tryptophan, or phenylalanine.

In certain embodiments, the host cell expresses an operon encoding an AroE enzyme, an AroD enzyme, an AroB enzyme, an AroG enzyme, a PpsA enzyme, and a TktA enzyme that catalyze reactions leading to the production of shikimate from phosphoenolpyruvate (PEP) and erythrose-4-phosphate (E4P). Preferably, the host cell contains the shikimate substrates PEP and E4P, and produces the shikimate in the cell. Advantageously, the host cell produces shikimate in an amount greater than that of a corresponding cell lacking the recombinant operon.

In other embodiments, the host cell expresses an operon encoding a YdiB enzyme, an AroD enzyme, an AroB enzyme, an AroG enzyme, a PpsA enzyme, and a TktA enzyme that catalyze reactions leading to the production of dehydroshikimate, dehydroquinate, and/or quinate from phosphoenolpyruvate (PEP) and erythrose-4-phosphate (E4P). Preferably, the host cell contains the shikimate substrates PEP and E4P, and produces the dehydroshikimate, dehydroquinate, and/or quinate in the cell. Advantageously, the host cell produces dehydroshikimate, dehydroquinate, and/or quinate in an amount greater than that of a corresponding cell lacking the recombinant operon.

In further embodiments, the host cell expresses an operon encoding a TyrB enzyme, a TyrA enzyme, an AroC enzyme, an AroA enzyme, and an AroL or AroK enzyme that catalyze reactions leading to the production of tyrosine from shikimate and/or shikimate intermediate. Additionally, the host cell may further contain and express the recombinant operon encoding the enzymes that catalyze reactions leading to the production of shikimate, or dehydroshikimate, dehydroquinate, and/or quinate from PEP and E4P. In certain preferred embodiments, the host cell contains the shikimate substrate and produces the tyrosine in the cell. Advantageously, the host cell produces tyrosine in an amount greater than that of a corresponding cell lacking the recombinant operon.

In other embodiments, the host cell expresses an operon encoding a TrpB or TrpA enzyme, a TrpC enzyme, a TrpD enzyme, a TrpE enzyme, an AroC enzyme, an AroA enzyme, and an AroL or AroK enzyme that catalyze reactions leading to the production of tryptophan from shikimate. Additionally, the host cell may further contain and express the recombinant operon encoding the enzymes that catalyze reactions leading to the production of shikimate, or dehydroshikimate, dehydroquinate, and/or quinate from PEP and E4P. In certain preferred embodiments, the host cell contains the shikimate substrate and produces the tryptophan in the cell. Advantageously, the host cell produces tryptophan in an amount greater than that of a corresponding cell lacking the recombinant operon.

In still other embodiments, the host cell expresses an operon encoding a TyrB enzyme, a PheA enzyme, an AroC enzyme, an AroA enzyme, and an AroL or AroK enzyme that catalyze reactions leading to the production of phenylalanine from shikimate. Additionally, the host cell may further contain and express the recombinant operon encoding the enzymes that catalyze reactions leading to the production of shikimate, or dehydroshikimate, dehydroquinate, and/or quinate from PEP and E4P. In certain preferred embodiments, the host cell contains the shikimate substrate and produces the phenylalanine in the cell. Advantageously, the host cell produces phenylalanine in an amount greater than that of a corresponding cell lacking the recombinant operon.

Shikimate Biosynthetic Pathway

Certain aspects of the present disclosure relate to host cells that recombinantly express a shikimate biosynthetic pathway by expressing the enzymes necessary for the production of shikimate and/or shikimate intermediates from phosphoenolpyruvate and erythrose-4-phosphate.

For example, a shikimate biosynthetic pathway of the present disclosure may include the production of erythrose-4-phosphate (E4P) from fructose-6-phosphate and glyceraldehyde-3-phosphate, the production of phosphoenolpyruvate (PEP) from the phosphorylation of pyruvate, the production of 3-deoxy-D-arabinoheptulosonate-7-phosphate (DAHP) from PEP and E4P, the conversion of DAHP to dehydroquinate (DHQ), the conversion of DHQ to 3-dehydroshikimate, and the conversion of 3-dehydroshikimate to shikimate (FIG. 1). In this biosynthetic pathway, the enzymes necessary for the production of shikimate and/or shikimate intermediates include, without limitation, a transketolase, a phosphoenolpyruvate synthase, a DAHP synthase, a DHQ synthase, a DHQ dehydratase, and a quinate/shikimate dehydrogenase.

Accordingly, in certain embodiments, host cells of the present disclosure contain a recombinant polynucleotide containing an operon encoding the enzymes necessary for the production of shikimate and/or shikimate intermediates from phosphoenolpyruvate (PEP) and erythrose-4-phosphate (E4P).

It has been shown that genes close to a regulatory sequence, such as a promoter are generally induced at much higher rates than those distal from the regulatory sequence. Without wishing to be bound by theory, it is believed that this reverse arrangement would create a metabolic flux pull towards the product by increasing protein concentration of the enzymes occurring in the latter part of the pathway. Thus, in certain preferred embodiments, all of the shikimate biosynthesis enzyme-encoding genes in the operon are arranged in an order that is opposite to that of the shikimate biosynthesis mechanism.

Transketolases

Suitable transketolases of the present disclosure catalyze the conversion of D-fructose-6-phophate and D-glyceraldehyde-3-phosphate to D-erythrose-4-phosphate and D-xylulose-5-phophate (E.C. 2.2.1.1). Examples of suitable transketolase enzymes include, without limitation, glycolaldehyde transferase, TK, and sedoheptulose-7-phosphate:D-glyceraldehyde-3-phosphate glycoaldehydetransferase.

Further examples of suitable transketolase enzymes include, without limitation, the *E. coli* enzyme TktA, paralogs thereof, homologs thereof, and orthologs thereof.

Phosphoenolpyruvate Synthases

Suitable phosphoenolpyruvate synthases of the present disclosure catalyze the phosphorylation of pyruvate to phosphoenolpyruvate (E.C. 2.7.9.2). Examples of suitable phosphoenolpyruvate synthase enzymes include, without limitation, PEP synthases, PEP synthetases, pyruvate, water dikinases, pyruvate-water dikinases, phosphoenolpyruvate synthases, phoephenolpyruvate synthetases, phosphoenolpyruvic synthases, and phosphopyruvate synthetases.

Further examples of suitable phosphoenolpyruvate synthase enzymes include, without limitation, the *E. coli* enzyme PpsA, paralogs thereof, homologs thereof, and orthologs thereof.

DAHP Synthases

Suitable 3-deoxy-D-arabinoheptulosonate-7-phosphate (DAHP) synthases of the present disclosure catalyze the formation of DAHP from phosphoenolpyruvate and erythrose-4-phosphate (E.C. 2.5.1.54). Examples of suitable DAHP synthase enzymes include, without limitation, 2-dehydro-3-deoxy-phosphoheptonate aldolases, 2-keto-3-deoxy-D-arabino-heptonic acid 7-phosphate synthetases, 3-deoxy-D-arabino-2-heptulosonic acid 7-phosphate synthetases, 3-deoxy-D-arabino-heptolosonate-7-phosphate synthetases, 3-deoxy-D-arabino-heptulosonate 7-phosphate synthetases, 7-phospho-2-keto-3-deoxy-D-arabino-heptonate D-erythrose-4-phosphate lyases, 7-phospho-2-dehydro-3-deoxy-D-arabino-heptonate D-erythrose-4-phosphate lyases, D-erythrose-4-phosphate-lyase; D-erythrose-4-phosphate-lyases, DAH7-P synthases, DAHP synthases, DS-Cos, DS-Mns, KDPH synthases, KDPH synthetases, deoxy-D-arabino-heptulosonate-7-phosphate synthetases, phospho-2-dehydro-3-deoxyheptonate aldolases, phospho-2-keto-3-deoxyheptanoate aldolases, phospho-2-keto-3-deoxyheptonate aldolases, phospho-2-keto-3-deoxyheptonic aldolases, and phospho-2-oxo-3-deoxyheptonate aldolases.

Further examples of suitable DAHP synthase enzymes include, without limitation, the *E. coli* enzyme AroG, paralogs thereof, homologs thereof, and orthologs thereof. In some embodiments, the AroG enzyme is a shikimate biosynthesis pathway feedback-resistant mutant. Techniques for generating mutations in enzyme-encoding genes are well known in the art, and include without limitation, random mutagenesis and screening, site-directed mutagenesis, PCR mutagenesis, insertional mutagenesis, chemical mutagenesis, and irradiation. Preferably, the AroG enzyme-encoding gene has been mutated such that the AroG enzyme contains a point mutation. In certain embodiments, the point mutation is an aspartate (Asp) to asparagine (Asn) point mutation. Preferably, the AroG enzyme is the *E. coli* AroG enzyme and the Asp to Asn point mutation is located at position 146 of the polypeptide sequence. In other embodiments, the AroG enzyme is a paralog, homolog, or ortholog of the *E. coli* AroG enzyme and the Asp to Asn point mutation is located at a position on the polypeptide sequence corresponding to position 146 of the *E. coli* AroG polypeptide sequence.

Dehydroquinate Synthases

Suitable dehydroquinate (DHQ) synthases of the present disclosure catalyze the NAD$^+$-dependent conversion of 3-deoxy-arabino-heptulosonate 7-phosphate to 3-dehydroquinate (E.C. 4.2.3.4). Examples of suitable dehydroquinate synthase enzymes include, without limitation, 3-dehydroquinate synthases, 5-dehydroquinate synthases, 5-dehydroquinic acid synthetases, dehydroquinate synthases, 3-dehydroquinate synthetases, 3-deoxy-arabino-heptulosonate-7-phosphate phosphate-lyases, 3-deoxy-arabino-heptulonate-7-phosphate phosphate-lyases, and 3-deoxy-arabinoheptulonate-7-phosphate phosphate-lyases.

Further examples of suitable dehydroquinate synthase enzymes include, without limitation, the *E. coli* enzyme AroB, paralogs thereof, homologs thereof, and orthologs thereof. In some embodiments, the AroB enzyme-encoding gene is codon optimized to increase expression of the enzyme. In certain preferred embodiments, rare codons located within the first 15 codons of the *E. coli* AroB enzyme-encoding gene or within the codons of paralogs, homologs, or orthologs of *E. coli* AroB enzyme-encoding genes corresponding to the first 15 codons of the *E. coli* AroB enzyme-encoding gene are codon optimized for expression in the host cell. Techniques for optimizing codons are well known in the art.

Dehydroquinate Dehydratases

Suitable dehydroquinate (DHQ) dehydratases of the present disclosure catalyze the dehydration of 3-dehydroquinate to 3-dehydroshikimate (E.C. 4.2.1.10). Examples of suitable dehydroquinate dehydratase enzymes include, without limitation, 3-dehydroquinate dehydratases, 3-dehydroquinate hydrolases, DHQases, dehydroquinate dehydratases, 3-dehydroquinases, 5-dehydroquinases, dehydroquinases, 5-dehydroquinate dehydratases, 5-dehydroquinate hydro-lyases, and 3-dehydroquinate hydro-lyases.

Further examples of suitable dehydroquinate dehydratase enzymes include, without limitation, the *E. coli* enzyme AroD, paralogs thereof, homologs thereof, and orthologs thereof.

Quinate/Shikimate Dehydrogenases

Suitable quinate/shikimate dehydrogenases of the present disclosure catalyze the NADPH-dependent reduction of 3-dehydroshikimate to shikimate (E.C. 1.1.1.25). Examples of suitable quinate/shikimate dehydrogenase enzymes include, without limitation, shikimate dehydrogenases, dehydroshikimic reductases, shikimate oxidoreductases, shikimate:NADP+ oxidoreductases, 5-dehydroshikimate reductases, shikimate 5-dehydrogenases, 5-dehydroshikimic reductases, DHS reductases, and shikimate:NADP+ 5-oxidoreductases.

Further examples of suitable quinate/shikimate dehydrogenase enzymes include the *E. coli* enzyme AroE, paralogs thereof, homologs thereof, and orthologs thereof. In certain embodiments, a recombinant operon of the present disclosure encoding the enzymes necessary for the production of shikimate, encodes the AroE enzyme, paralogs thereof, homologs thereof, or orthologs thereof. Advantageously, expression of the AroE paralog YdiB can result in the accumulation of the shikimate intermediates dehydroquinate (DHQ) and dehydroshikimate (DHS), as well as the shikimate side product quinate. Accordingly, in certain embodiments, a recombinant operon of the present disclosure encoding the enzymes necessary for the production of shikimate and/or shikimate intermediates, encodes the *E. coli* YdiB enzyme, paralogs thereof, homologs thereof, or orthologs thereof.

Shikimate Biosynthesis Pathway Operons

Operons of the present disclosure encoding the enzymes necessary for the production of shikimate or a shikimate intermediate may further include a regulatory sequence (e.g., promoters, enhancers, operators, terminators, etc.) to direct synthesis of the encoded enzymes.

In certain embodiments, the regulatory sequence, such as a promoter, is operably linked to the operon, thereby initiating transcription of the enzyme-encoding sequences via an RNA polymerase enzyme. Such promoters can be derived from microbial or viral sources, including CMV and SV40. Depending on the host/vector system utilized, any of a number of suitable transcription and translation control elements, including constitutive and inducible promoters, transcription enhancer elements, transcription terminators, etc. may be utilized (e.g., Bitter et al., *Methods in Enzymology*, 153:516-544, 1987).

Suitable promoters that may be used with host cells of the present disclosure include, without limitation, viral promoters, bacterial promoters, mammalian promoters, or plant promoters. Such promoters may be constitutive promoters, inducible promoters, or regulated promoters, such as environmentally-regulated or chemically-regulated promoters.

Suitable promoters for use in bacterial host cells include, without limitation, promoters capable of recognizing the T4, T3, Sp6, and T7 polymerases, the $P_R$ and $P_L$ promoters of bacteriophage lambda, the trp promoter of *E. coli*, recA promoter of *E. coli*, heat shock promoter of *E. coli*, and lacZ promoter of *E. coli*, the trc promoter, the tac promoter, the alpha-amylase promoter of *B. subtilis*, the sigma-specific promoter of *B. subtilis*, the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Bacterial promoters are reviewed by Glick, J. *Ind. Microbiol.* 1:277, 1987; Watson et al., Molecular Biology of the Gene, 4$^{th}$ Ed., Ilenjamin Cummins (1987); and Sambrook et al. (1989) Molecular Cloning: A Laboratory Manual, 2$^{nd}$ Ed., Cold Spring Harbor, N.Y.

Inducible promoters suitable for use in bacterial host cells are well known in the art, and include, without limitation, promoters that are affected by proteins, metabolites, or chemicals. Examples of such inducible promoter include, without limitation, a bovine leukemia virus promoter, a metallothionein promoter, a dexamethasone-inducible MMTV promoter, a SV40 promoter, a MRP polIII promoter, a tetracycline-inducible CMV promoter (such as the human immediate-early CMV promoter), promoters from the trp and lac operons, the inducible promoter $P_{lac-UV5}$, and the inducible promoter $P_{TRC}$.

Constitutive promoters suitable for use in bacterial host cells are well known in the art, and include, without limitation, constitutive adenovirus major late promoter, a constitutive MPSV promoter, a constitutive CMV promoter, and the constitutive promoter $P_{LtetO-1}$.

In certain embodiments, the regulatory sequence is located upstream (i.e., 5') of the operon. Preferably, the regulatory sequence is an inducible promoter. More preferably, the regulatory sequence is the $P_{lac-UV5}$ promoter. The $P_{lac-UV5}$ promoter is a mutated version of the lac promoter whose basal activity is less sensitive to intracellular levels of cyclic AMP.

In other embodiments, the operon contains a second regulatory sequence upstream of one of enzyme-encoding genes in the operon. Preferably, the second regulatory sequence is a constitutive promoter. In some embodiments, the second regulatory sequence is the $P_{Ltet-01}$ promoter. Preferably, the second regulatory sequence is located after (i.e., 3') of the gene encoding the DAHP synthase enzyme (e.g., AroG enzyme). As disclosed herein, it was found that inserting an *E. coli* rrnB T1-terminator 5' of the trc promoter prevents read-through and increases enzyme production. Accordingly in certain embodiments, the second regulatory sequence is a T1-$P_{TRC}$ terminator-promoter combination located after (i.e., 3') of the gene encoding the DAHP synthase enzyme (e.g., AroG enzyme).

Aromatic Amino Acid Biosynthetic Pathway

Other aspects of the present disclosure relate to host cells that recombinantly express an aromatic amino acid biosynthetic pathway by expressing the enzymes necessary for the production of an aromatic amino acid from shikimate and/or shikimate intermediates.

Suitable aromatic amino acids produced by the host cells of the present disclosure include, without limitation, tyrosine, tryptophan, and phenylalanine. Aromatic amino acids of the present disclosure may be either L-amino acids or D-amino acids. Preferably, host cells of the present disclosure produce an L-aromatic amino acid from shikimate.

Aromatic amino acid biosynthetic pathways of the present disclosure generally contain the final three enzyme-catalyzed reactions of the shikimate pathway. These three reactions are catalyzed by shikimate kinase enzymes, 5-enolpyruvylshikimate-3-phosphate (EPSP) synthase enzymes, and chorismate synthase enzymes. The final product of the shikimate pathway is chorismate. As disclosed herein, chorismate is an intermediate in the biosynthesis of aromatic amino acids such as tyrosine, tryptophan, and phenylalanine. In addition to the final three steps of the shikimate pathway, the aromatic amino acid biosynthetic pathways of the present disclosure further include the specific enzyme-catalyzed reactions necessary for the production of, for example, tyrosine, tryptophan, or phenylalanine.

An aromatic amino acid biosynthetic pathway of the present disclosure may be a tyrosine biosynthetic pathway. For example, a tyrosine biosynthetic pathway of the present disclosure may include the production of prephenate from chorismate, the production of 4-hydroxyphenylpyruvate from prephenate, and the production of tyrosine from 4-hydroxyphenylpyruvate (FIG. 1). In this biosynthetic pathway, the enzymes necessary for the production of tyrosine include, without limitation, a chorismate mutase, a prephenate dehydrogenase, and an aromatic amino acid aminotransferase.

Figure 4:
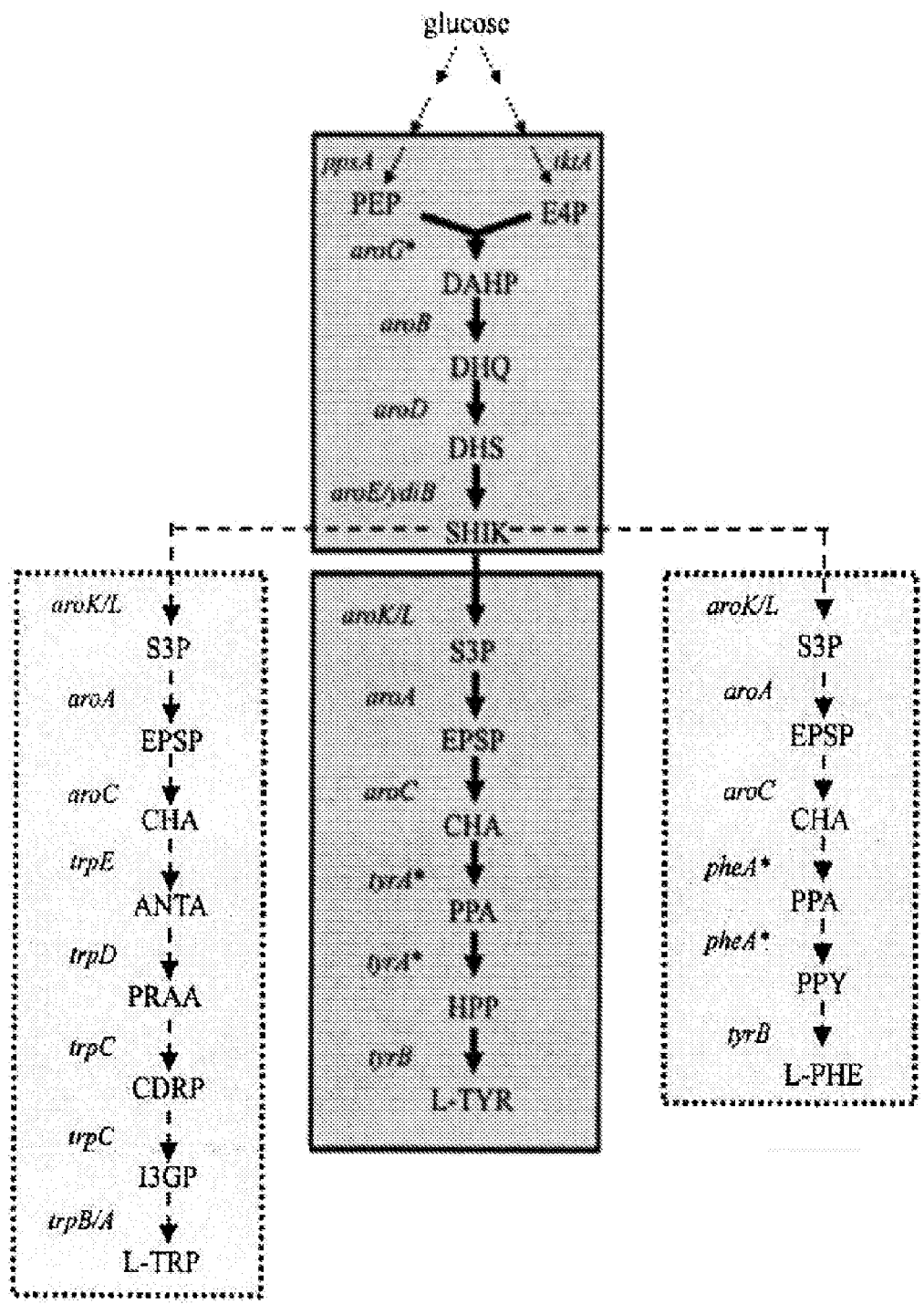
FIG. 4 depicts a redesign of the shikimate pathway using four operon modules. Instead of branching naturally at the chorismate, the redesigned pathway splits at shikimate. The upper module is for production of shikimate from glucose; the lower modules from left to right are for the production of tryptophan, tyrosine, and phenylalanine, respectively, when combined with the upper shikimate module. Notations for all abbreviations can be found in Bongaerts et al., *Metab Eng* 3:289-3002001, 2001.

An aromatic amino acid biosynthetic pathway of the present disclosure may also be a tryptophan biosynthetic pathway. For example, a tryptophan biosynthetic pathway of the present disclosure may include the production of anthranilate from chorismate, the production of N-(5-phospho-D-ribosyl)-anthranilate from anthranilate, the production of 1-(2-carboxyphenylamino)-1-deoxy-D-ribulose 5-phosphate from N-(5-phospho-D-ribosyl)-anthranilate, the production of indole-3-glycerol phosphate (IGP) from 1-(2-carboxyphenylamino)-1-deoxy-D-ribulose 5-phosphate, the production of indole from IGP, and the production of tryptophan from indole (FIG. 4). In this biosynthetic pathway, the enzymes necessary for the production of tryptophan include, without limitation, an anthranilate phosphoribosyl-transferase, an anthranilate synthase, a phosphoribosylanthranilate isomerase, an indole-3-glycerol-phosphate synthase, and a tryptophan synthase.

An aromatic amino acid biosynthetic pathway of the present disclosure may further be a phenylalanine biosynthetic pathway. For example, a phenylalanine biosynthetic pathway of the present disclosure may include the production of prephenate from chorismate, the production of phenylpyruvate from prephenate, and the production of phenylalanine from phenylpyruvate (FIG. 4). In this biosynthetic pathway, the enzymes necessary for the production of phenylalanine include, without limitation, a chorismate mutase enzyme, a prephenate dehydratase enzyme, and an aromatic amino acid aminotransferase enzyme.

Accordingly, in some embodiments, host cells of the present disclosure contain a recombinant polynucleotide containing an operon encoding the enzymes necessary for the production of an aromatic amino acid from shikimate and/or shikimate intermediates. In certain preferred embodiments, host cells of the present disclosure contain a recombinant polynucleotide containing an operon encoding the enzymes necessary for the production of tyrosine from shikimate and/or shikimate intermediates. Alternatively, host cells of the present disclosure may contain a recombinant polynucleotide containing an operon encoding the enzymes necessary for the production of tryptophan from shikimate and/or shikimate intermediates; or may contain a recombinant polynucleotide containing an operon encoding the enzymes necessary for the production of phenylalanine from shikimate and/or shikimate intermediates.

It has been shown that genes close to a regulatory sequence, such as a promoter are generally induced at much higher rates than those distal from the regulatory sequence. Without wishing to be bound by theory, it is believed that this reverse arrangement would create a metabolic flux pull towards the product by increasing protein concentration of the enzymes occurring in the latter part of the pathway.

Thus, in certain preferred embodiments, all of the aromatic amino acid biosynthesis enzyme-encoding genes in the operon are arranged in an order that is opposite to that of the aromatic amino acid biosynthesis mechanism, such as the tyrosine biosynthesis mechanism, the tryptophan biosynthesis mechanism, or the phenylalanine biosynthesis mechanism.

Shikimate Kinases

Suitable shikimate kinases of the present disclosure catalyze the ATP-dependent phosphorylation of shikimate to form 3-phosphoshikimate (E.C. 2.7.1.71). Examples of suitable shikimate kinase enzymes include, without limitation, shikimate kinase I enzymes, shikimate kinase II enzymes, and ATP:shikimate 3-phosphotransferases.

Further examples of suitable shikimate kinase enzymes include, without limitation, the $E.\ coli$ enzyme AroK, paralogs thereof, homologs thereof, and orthologs thereof; and the $E.\ coli$ enzyme AroL, which is an isozyme of AroK, paralogs thereof, homologs thereof, and orthologs thereof.

EPSP Synthases

Suitable 5-enolpyruvylshikimate-3-phosphate (EPSP) synthases of the present disclosure catalyze the conversion of phosphoenolpyruvate (PEP) and 3-phosphoshikimate to EPSP (E.C. 2.5.1.19). Examples of suitable EPSP synthase enzymes include, without limitation, 5-enolpyruvylshikimate-3-phosphate synthases, 3-enolpyruvylshikimate 5-phosphate synthases, 3-enolpyruvylshikimic acid-5-phosphate synthetases, 5'-enolpyruvylshikimate-3-phosphate synthases, 5-enolpyruvyl-3-phosphoshikimate synthases, 5-enolpyruvylshikimate-3-phosphate synthetases, 5-enolpyruvylshikimate-3-phosphoric acid synthases, enolpyruvylshikimate phosphate synthases, EPSP synthases, and phosphoenolpyruvate:3-phosphoshikimate 5-O-(1-carboxyvinyl)-transferases.

Further examples of suitable EPSP synthase enzymes include, without limitation, the $E.\ coli$ enzyme AroA, paralogs thereof, homologs thereof, and orthologs thereof.

Chorismate Synthases

Suitable chorismate synthases of the present disclosure catalyze the dephosphorylation of EPSP to form chorismate (E.C. 4.2.3.5). Examples of suitable chorismate synthase enzymes include, without limitation, 5-O-(1-carboxyvinyl)-3-phosphoshikimate phosphate-lyases, and 5-O-(1-carboxyvinyl)-3-phosphoshikimate phosphate-lyase (chorismate-forming) enzymes.

Further examples of suitable chorismate synthase enzymes include, without limitation, the $E.\ coli$ enzyme AroC, paralogs thereof, homologs thereof, and orthologs thereof.

Chorismate Mutases

Suitable chorismate mutases of the present disclosure catalyze the conversion of chorismate to prephenate (E.C. 5.4.99.5). Examples of suitable chorismate mutase enzymes include, without limitation, type I chorismate mutases, type II chorismate mutases, hydroxyphenylpyruvate synthases, chorismate pyruvatemutases, and chorismate mutase-prephenate dehydrogenase bifunctional enzymes.

Further example of a suitable chorismate mutase enzyme includes, without limitation, the $E.\ coli$ enzyme TyrA, and the $E.\ coli$ enzyme PheA. The $E.\ coli$ enzyme TyrA is a bifunctional enzyme that has an N-terminal type II chorismate mutase domain that has chorismate mutase activity. The $E.\ coli$ enzyme PheA is a bifunctional enzyme that has an N-terminal type II chorismate mutase domain that has chorismate mutase activity.

Accordingly, in certain embodiments, a recombinant operon of the present disclosure encoding the enzymes necessary for the production of tyrosine, encodes the *E. coli* TyrA enzyme, paralogs thereof, homologs thereof, or orthologs thereof. In other embodiments, a recombinant operon of the present disclosure encoding the enzymes necessary for the production of phenylalanine, encodes the *E. coli* PheA enzyme, paralogs thereof, homologs thereof, or orthologs thereof.

Prephenate Dehydrogenases

Suitable prephenate dehydrogenases of the present disclosure catalyze the oxidative decarboxylation of prephenate to from 4-hydroxyphenylpyruvate (E.C. 1.3.1.12). Examples of suitable prephenate dehydrogenase enzymes include, without limitation, hydroxyphenylpyruvate synthases, prephenate:NAD+ oxidoreductases, and chorismate mutase-prephenate dehydrogenase bifunctional enzymes.

A further example of a suitable prephenate dehydrogenase enzyme includes, without limitation, the *E. coli* enzyme TyrA, paralogs thereof, homologs thereof, and orthologs thereof. The *E. coli* enzyme TyrA is a bifunctional enzyme that has a prephenate dehydrogenase domain that has prephenate dehydrogenase activity.

TyrA Enzymes

In certain embodiments, an operon of the present disclosure encoding the enzymes necessary for producing tyrosine encodes the *E. coli* enzyme TyrA, paralogs thereof, homologs thereof, and orthologs thereof.

In some embodiments, the TyrA enzyme is a tyrosine biosynthesis pathway feedback-resistant mutant. Techniques for generating mutations in enzyme-encoding genes are well known in the art, and include without limitation, random mutagenesis and screening, site-directed mutagenesis, PCR mutagenesis, insertional mutagenesis, chemical mutagenesis, and irradiation. Preferably, the TyrA enzyme-encoding gene has been mutated such that the TyrA enzyme contains at least one point mutation. In certain embodiments, the at least one point mutation is a methionine (Met) to isoleucine (Ile) point mutation. Preferably, the TyrA enzyme is the *E. coli* TyrA enzyme and the Met to Ile point mutation is located at position 53 of the polypeptide sequence. In other embodiments, the TyrA enzyme is a paralog, homolog, or ortholog of the *E. coli* TyrA enzyme and the Met to Ile point mutation is located at a position on the polypeptide sequence corresponding to position 53 of the *E. coli* TyrA polypeptide sequence.

In other embodiments, the at least one point mutation is an alanine (Ala) to valine (Val) point mutation. Preferably, the TyrA enzyme is the *E. coli* TyrA enzyme and the Ala to Val point mutation is located at position 354 of the polypeptide sequence. In other embodiments, the TyrA enzyme is a paralog, homolog, or ortholog of the *E. coli* TyrA enzyme and the Ala to Val point mutation is located at a position on the polypeptide sequence corresponding to position 354 of the *E. coli* TyrA polypeptide sequence.

Preferably, the TyrA enzyme contains two point mutations. More preferably, the two point mutations are a Met to Ile point mutation and an Ala to Val point mutation. In some embodiments, TyrA enzyme is the *E. coli* TyrA enzyme, the Met to Ile point mutation is located at position 53 of the polypeptide sequence, and the Ala to Val point mutation is located at position 354 of the polypeptide sequence. In other embodiments, the TyrA enzyme is a paralog, homolog, or ortholog of the *E. coli* TyrA enzyme, the Met to Ile point mutation is located at a position on the polypeptide sequence corresponding to position 53 of the *E. coli* TyrA polypeptide sequence, and the Ala to Val point mutation is located at a position on the polypeptide sequence corresponding to position 354 of the *E. coli* TyrA polypeptide sequence.

Aromatic Amino Acid Aminotransferases

Suitable aromatic amino acid aminotransferases of the present disclosure catalyze the reversible conversion of an aromatic amino acid and 2-oxoglutarate to an aromatic oxo acid and L-glutamate (E.C. 2.6.1.57). In certain embodiments, an amino acid aminotransferase of the present disclosure catalyzes the conversion of 4-hydroxyphenylpyruvate and L-glutamate to tyrosine. In other embodiments, an amino acid aminotransferase of the present disclosure catalyzes the conversion of phenylpyruvate to phenylalanine. Examples of suitable aromatic amino acid aminotransferase enzymes include, without limitation, aromatic-amino-acid transaminases, aromatic aminotransferases, ArAT enzymes, and aromatic-amino-acid:2-oxoglutarate aminotransferases.

Further examples of suitable aromatic amino acid aminotransferase enzymes include, without limitation, the *E. coli* enzyme TyrB, paralogs thereof, homologs thereof, and orthologs thereof.

Tryptophan Synthases

Suitable tryptophan synthases of the present disclosure contain an α-subunit that catalyzes the reversible formation of indole and glyceraldehyde-3-phosphate (G3P) from indole-3-glycerol phosphate (IGP); and a β-subunit that catalyzes the irreversible pyridoxal phosphate-dependent condensation of indole and serine to form tryptophan (E.C. 4.2.1.20). Examples of suitable tryptophan synthase enzymes include, without limitation, L-tryptophan synthetases, indoleglycerol phosphate aldolases, tryptophan desmolases, tryptophan synthetases, L-serine hydro-lyases, and L-serine hydro-lyase [adding 1-C-(indol-3-yl)glycerol 3-phosphate, L-tryptophan and glyceraldehyde-3-phosphate-forming] enzymes.

Further examples of suitable tryptophan synthase enzymes include, without limitation, the *E. coli* enzyme TrpA, which is a tryptophan synthase α-subunit; and the *E. coli* enzyme TrpB, which is a tryptophan synthase β-subunit. In certain embodiments, the tryptophan synthase is the *E. coli* enzyme TrpA, paralogs thereof, homologs thereof, and orthologs thereof. In other embodiments, the tryptophan synthase is the *E. coli* enzyme TrpB, paralogs thereof, homologs thereof, and orthologs thereof.

Indole-3-glycerol-phosphate Synthases

Suitable indole-3-glycerol-phosphate synthases of the present disclosure catalyze the conversion of 1-(2-carboxyphenylamino)-1-deoxy-D-ribulose 5-phosphate to IGP (E.C. 4.1.1.48). Examples of suitable indole-3-glycerol-phosphate synthase enzymes include, without limitation, IGPS enzymes, indoleglycerol phosphate synthetased, indoleglycerol phosphate synthases, indole-3-glycerophosphate synthases, 1-(2-carboxyphenylamino)-1-deoxy-D-ribulose-5-phosphate carboxy-lyases, 1-(2-carboxyphenylamino)-1-deoxy-D-ribulose-5-phosphate carboxy-lyase [cyclizing; 1-C-(indol-3-yl)glycerol-3-phosphate-forming] enzymes, and IGPS:PRAI (indole-3-glycerol-phosphate synthetase/N-5'-phosphoribosylanthranilate isomerase complex) bifunctional enzymes.

A further example of a suitable indole-3-glycerol-phosphate synthase enzyme includes, without limitation, the *E. coli* enzyme TrpC, paralogs thereof, homologs thereof, and orthologs thereof. The *E. coli* enzyme TrpC is a bifunctional enzyme that has an N-terminal indole-3-glycerol-phosphate synthase domain that has indole-3-glycerol-phosphate synthase activity.

Phosphoribosylanthranilate Isomerases

Suitable phosphoribosylanthranilate isomerases of the present disclosure catalyze the conversion of N-(5-phospho-beta-D-ribosyl)-anthranilate to 1-(2-carboxyphenylamino)-

1-deoxy-D-ribulose 5-phosphate (E.C. 5.3.1.24). Examples of suitable phosphoribosylanthranilate isomerase enzymes include, without limitation, PRAI enzymes, PRA isomerases, N-(5-phospho-β-D-ribosyl)anthranilate ketol-isomerases, N-(5-phospho-β-D-ribosyl)anthranilate aldose-ketose-isomerases, and IGPS:PRAI (indole-3-glycerol-phosphate synthetase/N-5'-phosphoribosylanthranilate isomerase complex) bifunctional enzymes.

A further example of a suitable phosphoribosylanthranilate isomerase enzyme includes, without limitation, the *E. coli* enzyme TrpC, paralogs thereof, homologs thereof, and orthologs thereof. The *E. coli* enzyme TrpC is a bifunctional enzyme that has a C terminal phosphoribosylanthranilate isomerase domain that has phosphoribosylanthranilate isomerase activity.

Anthranilate Synthases

Suitable anthranilate synthases of the present disclosure contain a component I subunit that catalyzes the formation of anthranilate from ammonia rather than glutamine, and a component II subunit that provides glutamine aminidotransferase activity. Anthranilate synthases of the present disclosure catalyze the conversion of chorismate and L-glutamine to anthranilate, pyruvate, and L-glutamate (E.C. 4.1.3.27). Examples of suitable anthranilate synthase enzymes include, without limitation, anthranilate synthetases, chorismate lyases, and chorismate pyruvate-lyases.

Further examples of suitable anthranilate synthase enzymes include, without limitation, the *E. coli* enzyme TrpD, which is an anthranilate synthases component II subunit; and the *E. coli* enzyme TrpE, which is an anthranilate synthases component I subunit.

In certain embodiments, the anthranilate synthase is the *E. coli* enzyme TrpD, paralogs thereof, homologs thereof, and orthologs thereof. The *E. coli* enzyme TrpD is a bifunctional enzyme that has an N-terminal anthranilate synthases component II domain that has glutamine amidotransferase activity. In other embodiments, the anthranilate synthase is the *E. coli* enzyme TrpE, paralogs thereof, homologs thereof, and orthologs thereof.

Anthranilate Phosphoribosyltransferases

Suitable anthranilate phosphoribosyltransferases of the present disclosure catalyze the reversible conversion of N-(5-phospho-beta-D-ribosyl)-anthranilate to anthranilate (E.C. 2.4.2.18). In certain embodiments, anthranilate phosphoribosyltransferases of the present disclosure catalyze the production of N-(5-phospho-D-ribosyl)-anthranilate. Examples of suitable anthranilate phosphoribosyltransferase enzymes include, without limitation, phosphoribosyl-anthranilate pyrophosphorylases, PRT enzymes, anthranilate 5-phosphoribosylpyrophosphate phosphoribosyltransferases, anthranilate phosphoribosylpyrophosphate phosphoribosyltransferases, phosphoribosylanthranilate pyrophosphorylases, phosphoribosylanthranilate transferases, anthranilate-PP-ribose-P phosphoribosyltransferases, and N-(5-phospho-D-ribosyl)-anthranilate:diphosphate phospho-α-D-ribosyltransferases.

A further example of a suitable anthranilate phosphoribosyltransferase enzyme includes, without limitation, the *E. coli* enzyme TrpD, paralogs thereof, homologs thereof, and orthologs thereof. The *E. coli* enzyme TrpD is a bifunctional enzyme that has a C-terminal anthranilate phosphoribosyltransferase domain that has anthranilate phosphoribosyltransferase activity.

Prephenate Dehydratases

Suitable prephenate dehydratases of the present disclosure catalyze the dehydration of prephenate to form phenylpyruvate (E.C. 4.2.1.51). Examples of suitable prephenate dehydratase enzymes include, without limitation, prephenate hydro-lyases, and prephenate hydro-lyase (decarboxylating; phenylpyruvate-forming) enzymes.

Further examples of suitable prephenate dehydratase enzymes include, without limitation, the *E. coli* enzyme PheA, paralogs thereof, homologs thereof, and orthologs thereof. The *E. coli* enzyme PheA is a bifunctional enzyme that has a central prephenate dehydratase domain that has prephenate dehydratase activity.

Aromatic Amino Acid Biosynthesis Pathway Operons

Operons of the present disclosure encoding the enzymes necessary for the production of an aromatic amino acid may further include a regulatory sequence (e.g., promoters, enhancers, operators, terminators, etc.) to direct synthesis of the encoded enzymes.

In certain embodiments, the regulatory sequence, such as a promoter, is operably linked to the operon, thereby initiating transcription of the enzyme-encoding sequences via an RNA polymerase enzyme. Such promoters can be derived from microbial or viral sources, including CMV and SV40. Depending on the host/vector system utilized, any of a number of suitable transcription and translation control elements, including constitutive and inducible promoters, transcription enhancer elements, transcription terminators, etc. may be utilized (e.g., Bitter et al., *Methods in Enzymology*, 153:516-544, 1987).

Suitable promoters that may be used with host cells of the present disclosure include, without limitation, viral promoters, bacterial promoters, mammalian promoters, or plant promoters. Such promoters may be constitutive promoters, inducible promoters, or regulated promoters, such as environmentally-regulated or chemically-regulated promoters. Examples of suitable promoters include, without limitation, promoters capable of recognizing the T4, T3, Sp6, and T7 polymerases, the $P_R$ and $P_L$ promoters of bacteriophage lambda, the trp promoter of *E. coli*, recA promoter of *E. coli*, heat shock promoter of *E. coli*, and lacZ promoter of *E. coli*, the trc promoter, the tac promoter, the alpha-amylase promoter of *B. subtilis*, the sigma-specific promoter of *B. subtilis*, the promoters of the bacteriophages of *Bacillus*, *Streptomyces* promoters, the int promoter of bacteriophage lambda, the bla promoter of the beta-lactamase gene of pBR322, and the CAT promoter of the chloramphenicol acetyl transferase gene. Examples of inducible promoters include, without limitation, promoters that are affected by proteins, metabolites, or chemicals. Examples of such inducible promoter include, without limitation, a bovine leukemia virus promoter, a metallothionein promoter, a dexamethasone-inducible MMTV promoter, a SV40 promoter, a MRP polIII promoter, a tetracycline-inducible CMV promoter (such as the human immediate-early CMV promoter), promoters from the trp and lac operons, the inducible promoter $P_{lac}$-UV5, and the inducible promoter $P_{TRC}$. Examples of constitutive promoters include, without limitation, constitutive adenovirus major late promoter, a constitutive MPSV promoter, a constitutive CMV promoter, and the constitutive promoter $P_{LtetO-1}$.

In certain embodiments, the regulatory sequence is located upstream (i.e., 5') of the operon. Preferably, the regulatory sequence is an inducible promoter. More preferably, the regulatory sequence is the $P_{lac}$-UV5 promoter. In other embodiments, the operon contains a second regulatory sequence upstream of one of enzyme-encoding genes in the operon. Preferably, the second regulatory sequence is a constitutive promoter. In some embodiments, the second regulatory sequence is the $P_{Ltet}$-01 promoter or the T1-$P_{TRC}$ terminator-promoter combination. Preferably, the second regulatory sequence is located after (i.e., 3') of the gene encoding the chorismate synthase enzyme (e.g., AroC enzyme).

Methods of Producing and Culturing Host Cells

Other aspects of the present disclosure relate to the production of host cells that contain a recombinant polynucleotide containing an operon encoding the enzymes necessary for the production of shikimate and/or shikimate intermediate from phosphoenolpyruvate and erythrose-4-phosphate, and/or a recombinant polynucleotide containing an operon encoding the enzymes necessary for the production of an aromatic amino acid from shikimate and/or shikimate intermediate.

Each recombinant polynucleotide sequence of the present disclosure containing an operon encoding the enzymes necessary for the production of shikimate and/or shikimate intermediate, and containing an operon encoding the enzymes necessary for the production of an aromatic amino acid can be incorporated into an expression vector. An "expression vector" or "vector" refers to a compound and/or composition that transduces, transforms, or infects a host cell, thereby causing the cell to express polynucleotides and/or proteins other than those endogenous to the cell, or in a manner not naturally occurring in the cell. An expression vector contains a sequence of polynucleotides (ordinarily RNA or DNA) to be expressed by the host cell. Optionally, the expression vector also contains materials to aid in achieving entry of the polynucleotide into the host cell, such as a virus, liposome, protein coating, or the like. The expression vectors contemplated for use in the present disclosure include those into which a polynucleotide sequence can be inserted, along with any preferred or required operational elements. Further, the expression vector can be transferred into a host cell and replicated therein. Once transferred or transformed into a suitable host cell, the vector may replicate and function independently of the host genome, or may, in some instances, integrate into the genome itself. Examples of expression vectors include, without limitation, a plasmid, a phage particle, or simply a potential genomic insert. Preferred expression vectors are plasmids, particularly those with restriction sites that have been well-documented and that contain the operational elements preferred or required for transcription of the polynucleotide sequence. Such plasmids, as well as other expression vectors, are well known in the art.

Incorporation of the individual polynucleotide sequences may be accomplished through known methods that include, for example, the use of restriction enzymes (such as BamHI, EcoRI, Hhal, Xhol, Xmal, and so forth) to cleave specific sites in the expression vector, e.g., plasmid. The restriction enzyme produces single-stranded ends that may be annealed to a polynucleotide sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide sequence are often cleaved with the same restriction enzyme, thereby assuring that the ends of the expression vector and the ends of the polynucleotide sequence are complementary to each other. In addition, DNA linkers may be used to facilitate linking of polynucleotide sequences into an expression vector.

A series of individual polynucleotide sequences can also be combined by utilizing methods that are known in the art (e.g., U.S. Pat. No. 4,683,195). For example, each of the desired polynucleotide sequences can be initially generated in a separate PCR. Thereafter, specific primers are designed such that the ends of the PCR products contain complementary sequences. When the PCR products are mixed, denatured, and reannealed, the strands may have matching sequences at their 3' end overlap and can act as primers for each other. Extension of this overlap by DNA polymerase produces a molecule in which the original sequences are "spliced" together. In this way, a series of individual polynucleotide sequences may be "spliced" together and subsequently transduced into a host cell simultaneously. Thus, expression of each of the plurality of polynucleotide sequences is effected.

Individual polynucleotide sequences, or "spliced" polynucleotide sequences, are then incorporated into an expression vector. The present disclosure is not limited with respect to the process by which the polynucleotide sequence is incorporated into the expression vector. Those of ordinary skill in the art are familiar with the necessary steps for incorporating a polynucleotide sequence into an expression vector. A typical expression vector contains the desired polynucleotide sequence containing an operon of the present disclosure preceded by one or more regulatory sequences, along with a ribosome binding site, e.g., a nucleotide sequence that is 3-9 nucleotides in length and located 3-11 nucleotides upstream of the initiation codon in *E. coli* (see Shine et al. (1975), Nature 254:34 and Steitz, Biological Regulation and Development: Gene Expression (ed. R. F. Goldberger), vol. 1, p. 349, 1979, Plenum Publishing, NY). In certain embodiments, one or more additional regulatory sequences may be inserted downstream of one of the enzyme-encoding genes in the operon.

Regulatory sequences include, for example, those sequences that contain a promoter and an operator. A promoter is operably linked to the desired polynucleotide sequence, thereby initiating transcription of the polynucleotide sequence via an RNA polymerase enzyme. An operator is a sequence of polynucleotides adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. As disclosed herein, any suitable promoter, and operator may be used.

Copy number may also be controlled by the choice of expression vector used. For example, the expression vector may be a low copy number vector, a medium copy number vector, or a high copy number vector. In certain preferred embodiments, the expression vector is a medium copy number vector. Moreover, the origin of replication used in the expression vector may also determine the copy number. Any suitable origin of replication for controlling copy number known in the art may be used.

Although any suitable expression vector may be used to incorporate the desired polynucleotide sequences, readily-available expression vectors include, without limitation, plasmids, such as pAM2991, pSClO1, p15A, pZ21, pBbB5c, pRBS01, pRBA5a, pZA31, pBR322, pBBR1MCS-3, pUR, pEX, pMR1OO, pCR4, pBAD24, pUC19, and bacteriophages, such as M1 3 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the present disclosure may be introduced or transferred into a host cell of the present disclosure. Such methods for transferring the expression vectors into host cells are well known in the art. For example, one method for transforming bacteria with an expression vector involves a calcium chloride treatment wherein the expression vector is introduced via a calcium precipitate. Other salts, e.g., calcium phosphate, may also be used following a similar procedure. In addition, electroporation (i.e., the application of a current to increase the permeability of cells to nucleic acid sequences) may be used to transfect the host cell. Also, microinjection of the recombinant polynucleotides provides the ability to transfect host cells. Other means, such as lipid complexes, liposomes, and dendrimers, may also be employed. Those of ordinary skill in the art can transfect a host cell with a desired polynucleotide using these or other methods.

For identifying a transfected host cell, a variety of methods are available. For example, a culture of potentially transfected host cells may be separated, using a suitable dilution, into individual cells and thereafter individually grown and tested for expression of the desired polynucleotide sequence. In addition, when plasmids are used, an often-used practice involves the selection of cells based upon antimicrobial resistance that has been conferred by genes intentionally contained within the expression vector, such as the amp, gpt, neo, and hyg genes.

Once the host cell has been transformed with the expression vector, the host cell is allowed to grow. Methods of the present disclosure include culturing the host cell such that the recombinant polynucleotides in the cell are expressed. For bacterial host cells, this process entails culturing the cells in a suitable medium. Typically cells are grown at 35° C. in appropriate media. Preferred growth media in the present disclosure are common commercially prepared media such as Luria Ilertani (LB) broth, Sabouraud Dextrose (SD) broth or yeast medium (YM) broth. Other defined or synthetic growth media may also be used, and the appropriate medium for growth of the particular host cell will be known by someone skilled in the art.

According to some aspects of the present disclosure, the culture media contains a carbon source for the host cell. Such a "carbon source" generally refers to a substrate or compound suitable to be used as a source of carbon for prokaryotic or simple eukaryotic cell growth. Carbon sources can be in various forms, including, without limitation, polymers, carbohydrates, acids, alcohols, aldehydes, ketones, amino acids, peptides, etc. These include, for example, various monosaccharides, such as glucose, glucose, galactose, fructose, xylose, and arabinose; disaccharides, such as sucrose and lactose; oligosaccharides; polysaccharides; biomass polymers, such as cellulose and hemicellulose; saturated or unsaturated fatty acids; succinate; lactate; acetate; ethanol; etc.; or mixtures thereof.

In addition to an appropriate carbon source, culture media may contain minerals, salts, cofactors, buffers, and other components, known to those skilled in the art, suitable for the growth of the cell cultures and promotion of the enzymatic pathways necessary for production of shikimate, shikimate intermediates, and/or aromatic amino acids. Reactions may be performed under aerobic or anaerobic conditions where aerobic, anoxic, or anaerobic conditions are preferred based on the requirements of the host cell. As the host cell grows and/or multiplies, the enzymes necessary for producing shikimate, shikimate intermediates, and/or aromatic amino acids are expressed.

Methods of Producing Shikimate and Shikimate Intermediates

As disclosed herein, recombinant expression in a host cell of an operon encoding the enzymes necessary for the production of shikimate and/or a shikimate intermediate from phosphoenolpyruvate and erythrose-4-phosphate results in increased production of shikimate and/or shikimate intermediate in the host cell, as compared to a corresponding cell that does not recombinantly express the operon.

Accordingly, certain aspects of the present disclosure relate to methods of increasing production of a tyrosine intermediate in a host cell by providing a host cell of the present disclosure containing a recombinant polynucleotide that contains an operon encoding the enzymes necessary for the production of shikimate and/or a shikimate intermediate from phosphoenolpyruvate and erythrose-4-phosphate; and culturing the host cell in a medium such that the recombinant polynucleotide is expressed, where expression of the recombinant polynucleotide results in increased production of a tyrosine intermediate compared to a corresponding cell lacking the recombinant polynucleotide. Examples of conditions sufficient for the host cell to express the recombinant polynucleotide are well known in the art and disclosed herein. The tyrosine intermediate can be shikimate or a shikimate intermediate, such as dehydroshikimate, dehydroquinate, or quinate. Preferably, the tyrosine intermediate is shikimate.

In some embodiments, the host cell produces from about 50 mg/L to about 1,000 mg/L of shikimate. Preferably, the host cell produces from about 80 mg/L to about 760 mg/L of shikimate. More preferably, the host cell produces from about 79 mg/L to about 759 mg/L of shikimate. In other embodiments, the host cell produces at least about 50 mg/L, at least about 60 mg/L, at least about 70 mg/L, at least about 80 mg/L, at least about 90 mg/L, at least about 100 mg/L, at least about 150 mg/L, at least about 200 mg/L, at least about 250 mg/L, at least about 300 mg/L, at least about 350 mg/L, at least about 400 mg/L, at least about 450 mg/L, at least about 500 mg/L, at least about 550 mg/L, at least about 600 mg/L, at least about 650 mg/L, at least about 700 mg/L, at least about 750 mg/L, at least about 800 mg/L, at least about 850 mg/L, at least about 900 mg/L, at least about 950 mg/L, or at least about 1,000 mg/L of shikimate. Preferably, the host cell produces at least about 79 mg/L, at least about 194 mg/L, at least about 273 mg/L, at least about 278 mg/L, at least about 510 mg/L, or at least about 759 mg/L of shikimate.

In other embodiments, the host cell produces from about 50 mg/L to about 1,500 mg/L of dehydroshikimate. Preferably, the host cell produces from about 45 mg/L to about 1,230 mg/L of dehydroshikimate. More preferably, the host cell produces from about 46 mg/L to about 1,227 mg/L of dehydroshikimate. In other embodiments, the host cell produces at least about 40 mg/L, at least about 45 mg/L at least about 50 mg/L, at least about 100 mg/L, at least about 150 mg/L, at least about 200 mg/L, at least about 250 mg/L, at least about 300 mg/L, at least about 350 mg/L, at least about 400 mg/L, at least about 450 mg/L, at least about 500 mg/L, at least about 550 mg/L, at least about 600 mg/L, at least about 650 mg/L, at least about 700 mg/L, at least about 750 mg/L, at least about 800 mg/L, at least about 850 mg/L, at least about 900 mg/L, at least about 950 mg/L, at least about 1,000 mg/L, at least about 1,100 mg/L, at least about 1,200 mg/L, at least about 1,300 mg/L, at least about 1,400 mg/L, or at least about 1,500 mg/L of dehydroshikimate. Preferably, the host cell produces at least about 46 mg/L, at least about 70 mg/L, at least about 113 mg/L, at least about 588 mg/L, at least about 1,029 mg/L, or at least about 1,227 mg/L of dehydroshikimate.

In other embodiments, the host cell produces from about 1 mg/L to about 100 mg/L of dehydroquinate. Preferably, the host cell produces from about 3 mg/L to about 60 mg/L of dehydroquinate. More preferably, the host cell produces from about 4 mg/L to about 56 mg/L of dehydroquinate. In other embodiments, the host cell produces at least about 1 mg/L, at least 2 about mg/L at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 15 mg/L, at least about 20 mg/L, at least about 25 mg/L, at least about 30 mg/L, at least about 35 mg/L, at least about 40 mg/L, at least about 45 mg/L, at least about 50 mg/L, at least about 55 mg/L, at least about 60 mg/L, at least about 65 mg/L, at least about 70 mg/L, at least about 80 mg/L, at least about 85 mg/L, at least about 90 mg/L, at least about 95 mg/L, or at least about 100 mg/L of dehydroquinate. Preferably, the host cell produces at least about 4 mg/L, at least about 5 mg/L, at least about 8 mg/L, at least about 36 mg/L, at least about 51 mg/L, or at least about 56 mg/L of dehydroquinate.

In other embodiments, the host cell produces from about 1 mg/L to about 250 mg/L of quinate. Preferably, the host cell produces from about 2 mg/L to about 245 mg/L of quinate. More preferably, the host cell produces from about 2 mg/L to about 242 mg/L of quinate. In other embodiments, the host cell produces at least about 1 mg/L, at least about 2 mg/L at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 15 mg/L, at least about 20 mg/L, at least about 30 mg/L, at least about 40 mg/L, at least about 50 mg/L, at least about 60 mg/L, at least about 70 mg/L, at least about 80 mg/L, at least about 90 mg/L, at least about 100 mg/L, at least about 105 mg/L, at least about 110 mg/L, at least about 125 mg/L, at least about 150 mg/L, at least about 175 mg/L, at least about 200 mg/L, at least about 210 mg/L, at least about 220 mg/L, at least about 230 mg/L, at least about 240 mg/L, at least about 245 mg/L, or at least about 250 mg/L of quinate. Preferably, the host cell produces at least about 2 mg/L, at least about 3 mg/L, at least about 11 mg/L, at least about 106 mg/L, at least about 165 mg/L, or at least about 242 mg/L of quinate.

The shikimate and shikimate derivatives produced by the host cells and methods of the present disclosure find many uses including, without limitation, use as precursors in the production of aromatic amino acids; use as precursors in the production of animal feeds, food additives, and supplements; use as precursors in the production of commodity chemicals; and use as precursors in the production of pharmaceuticals. In certain embodiments, the shikimate and shikimate derivatives produced by the host cells and methods of the present disclosure find use as a precursor in the synthesis of antiviral drugs.

Methods of Producing Aromatic Amino Acids

As disclosed herein, recombinant expression in a host cell of an operon encoding the enzymes necessary for the production of an aromatic amino acid from shikimate and/or a shikimate intermediate results in increased production of the aromatic amino acid in the host cell, as compared to a corresponding cell that does not recombinantly express the operon.

Accordingly, certain aspects of the present disclosure relate to methods of increasing production of a tyrosine intermediate in a host cell by providing a host cell of the present disclosure containing a first recombinant polynucleotide that contains an operon encoding the enzymes necessary for the production of shikimate and/or a shikimate intermediate from phosphoenolpyruvate and erythrose-4-phosphate, and a second recombinant polynucleotide that contains an operon encoding the enzymes necessary for the production of an aromatic amino acid from shikimate and/or a shikimate intermediate; and culturing the host cell in a medium such that the first and second recombinant polynucleotides are expressed, where expression of the first and second recombinant polynucleotides results in increased production of an aromatic amino acid compared to a corresponding cell lacking the first and second recombinant polynucleotides. Examples of conditions sufficient for the host cell to express the first and second recombinant polynucleotides are well known in the art and disclosed herein. The aromatic amino acid can be tyrosine, tryptophan, or phenylalanine. Preferably, the aromatic amino acid is tyrosine. Additionally, the host cell may be a microorganism. Preferably, the host cell is an *E. coli* cell.

In some embodiments, the host cell produces from about 0.75 g/L to about 2.7 g/L of tyrosine. Preferably, the host cell produces from about from about 0.75 g/L to about 2.17 g/L of tyrosine. In other embodiments, the host cell produces at least about 0.75 g/L, at least about 0.8 g/L, at least about 0.9 g/L, at least about 1 g/L, at least about 1.15 g/L, at least about 1.22 g/L, at least about 1.25 g/L, at least about 1.31 g/L, at least about 1.5 g/L, at least, at least about 1.75 g/L, at least about 2 g/L, at least about 2.1 g/L, at least about 2.17 g/L, at least about 2.2 g/L, at least about 2.3 g/L, at least about 2.4 g/L, at least about 2.5 g/L, at least about 2.6 g/L, or at least about 2.7 g/L of tyrosine. Preferably, the host cell produces at least about 0.746 g/L, at least about 0.897 g/L, at least about 0.908 g/L, at least about 1.15 g/L, at least about 1.22 g/L, at least about 1.31 g/L, or at least about 2.17 g/L of tyrosine.

In other embodiments, the host cell produces a tyrosine yield that is from about 5% to about 220% greater than an amount of tyrosine produced by the corresponding cell lacking the first and second recombinant polynucleotides. Preferably, the host cell produces a tyrosine yield that is from about 6.5% to about 210% greater than an amount of tyrosine produced by the corresponding cell lacking the first and second recombinant polynucleotides. In further embodiments, the host cell produces a tyrosine yield that is at least about 5%, at least about 6%, at least about 7%, at least about 8%, at least about 10%, at least about 15%, at least about 20%, at least about 25%, at least about 26%, at least about 27%, at least about 28%, at least about 30%, at least about 35%, at least about 40%, at least about 45%, at least about 50%, at least about 55%, at least about 60%, at least about 61%, at least about 62%, at least about 63%, at least about 64%, at least about 65%, at least about 70%, at least about 71%, at least about 72%, at least about 73%, at least about 74%, at least about 75%, at least about 80%, at least about 85%, at least about 86%, at least about 87%, at least about 88%, at least about 89%, at least about 90%, at least about 95%, at least about 100%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, at least about 200%, at least about 205%, at least about 206%, at least about 207%, at least about 208%, at least about 210%, at least about 211%, at least about 212%, at least about 214%, at least about 215%, or at least about 220% greater than an amount of tyrosine produced by the corresponding cell lacking the first and second recombinant polynucleotides. Preferably, the host cell produces a tyrosine yield that is at least about 6.5%, at least about 28%, at least about 30%, at least about 64%, at least about 74%, at least about 87%, or at least about 210% greater than an amount of tyrosine produced by the corresponding cell lacking the first and second recombinant polynucleotides.

In other embodiments, the tyrosine is produced at a percentage yield that is from about 27% to about 95% of the theoretical maximal yield. Preferably, the tyrosine is produced at a percentage yield that is from about 27% to about 79% of the theoretical maximal yield. In further embodiments, the tyrosine is produced at a percentage yield that is at least about 27%, at least about 33%, at least about 40%, at least about 42%, at least about 44%, at least about 60%, at least about 65%, at least about 70%, at least about 75%, at least about 80%, at least about 90%, or at least about 95% of the theoretical maximal yield. Preferably, the tyrosine is produced at a percentage yield that is at least about 27%, at least about 33%, at least about 42%, at least about 44%, at least about 48%, or at least about 79% of the theoretical maximal yield.

In other embodiments, the tyrosine is produced at a percentage of the theoretical maximal yield that is from about 5% to about 220% greater than the percentage of the theoretical maximal yield of tyrosine produced by the corresponding cell lacking the first and second recombinant polynucleotides. Preferably, the tyrosine is produced at a percentage of the theoretical maximal yield that is from about 8% to about 216% greater than the percentage of the theoretical maximal yield of tyrosine produced by the corresponding cell lacking the first and second recombinant polynucleotides. In further embodiments, the tyrosine is produced at a percentage of the theoretical maximal yield that is at least about 5%, at least about 6%, at least about 7%, at least about 8%, at least about 10%, at least about 15%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 40%, at least about 45%, at least about 50%, at least about 55%, at least about 60%, at least about 65%, at least about 66%, at least about 67%, at least about 68%, at least about 69%, at least about 70%, at least about 75%, at least about 76%, at least about 77%, at least about 78%, at least about 79%, at least about 80%, at least about 85%, at least about 90%, at least about 91%, at least about 92%, at least about 93%, at least about 94%, at least about 95%, at least about 100%, at least about 110%, at least about 115%, at least about 120%, at least about 125%, at least about 130%, at least about 135%, at least about 140%, at least about 145%, at least about 150%, at least about 155%, at least about 160%, at least about 165%, at least about 170%, at least about 175%, at least about 180%, at least about 185%, at least about 190%, at least about 195%, at least about 200%, at least about 205%, at least about 210%, at least about 211%, at least about 212%, at least about 213%, at least about 214%, at least about 215%, at least about 216%, at least about 217%, at least about 218%, at least about 219%, or at least about 220% greater than the percentage of the theoretical maximal yield of tyrosine produced by the corresponding cell lacking the first and second recombinant polynucleotides. Preferably, the tyrosine is produced at a percentage of the theoretical maximal yield that is at least about 8%, at least about 32%, at least about 68%, at least about 76%, at least about 92%, or at least about 216% greater than the percentage of the theoretical maximal yield of tyrosine produced by the corresponding cell lacking the first and second recombinant polynucleotides.

In some embodiments, the host cell further contains and expresses the proteins necessary to produce a commodity chemical.

The aromatic amino acids produced by the host cells and methods of the present disclosure find many uses including, without limitation, use as animal feeds, use as food additives, use as supplements, use as precursors in the production of commodity chemicals, use as precursors in the production of pharmaceuticals, and use as precursors in the production of biopolymers.

Commodity Chemicals

Further aspects of the present disclosure relate to host cells of the present disclosure that recombinantly express an operon encoding the enzymes necessary for the production of shikimate and/or shikimate intermediate from phosphoenolpyruvate and erythrose-4-phosphate, and/or an operon encoding the enzymes necessary for the production of an aromatic amino acid from shikimate and/or shikimate intermediate, and that further produce commodity chemicals. Accordingly, in certain embodiments, host cells of the present disclosure that recombinantly express an operon encoding the enzymes necessary for the production of shikimate and/or shikimate intermediate from phosphoenolpyruvate and erythrose-4-phosphate, and/or an operon encoding the enzymes necessary for the production of an aromatic amino acid from shikimate and/or shikimate intermediate, further contain the proteins necessary to produce a commodity chemical. Other aspects of the present disclosure further relate to methods of utilizing such host cells to produce commodity chemicals.

Commodity chemicals include, without limitation, any saleable or marketable chemical that can be produced either directly or as a by-product of a host cell of the present disclosure. Examples of commodity chemicals include, without limitation, biofuels, polymers, specialty chemicals, and pharmaceutical intermediates. Biofuels include, without limitation, alcohols such as ethanol, propanol, isopropanol, acetone, butanol, isobutanol, 2-methyl-1-butanol, 3-methyl-1-butanol, phenylethanol, fatty alcohols, and isopentenol; aldehydes, such as acetylaldehyde, propionaldehyde, butyraldehyde, isobutyraldehyde, 2-methyl-1-butanal, 3-methyl-1-butanal, phenylacetaldehyde, and fatty aldehydes; hydrocarbons, such as alkanes, alkenes, isoprenoids, fatty acids, wax esters, and ethyl esters; and inorganic fuels such as hydrogen. Polymers include, without limitation, biopolymers, 1,3-propandiol, 1,4-butanediol, polyhydroxyalkanoate, polyhydroxybutyrate, and isoprene. Specialty chemicals include, without limitation, alkaloids, benzylisoquinoline alkaloids, carotenoids, such as lycopene, β-carotene, etc. Pharmaceutical intermediates include, without limitation, reticuline, polyketides, statins, omega-3 fatty acids, isoprenoids, steroids, and erythromycin (antibiotic). Further examples of commodity chemicals include, without limitation, lactate, succinate, glutamate, citrate, malate, 3-hydroxypropionate, ascorbate, sorbitol, amino acids (leucine, valine, isoleucine, etc.), and hydroxybutyrate.

In some embodiments, a host cell of the present disclosure produces one or more precursors necessary for the production of the desired commodity chemical. The genes encoding the desired enzymes may be heterologous to the host cell, or the genes may be endogenous to the host cell but operatively linked to heterologous promoters and/or control sequences that result in higher expression of the gene(s) in the host cell. For example, in certain embodiments, a host cell of the present disclosure may be further modified to overexpress metabolic genes involved in sugar digestion, including without limitation glycolytic, pentose phosphate, and tricarboxylic acid cycle genes.

In other embodiments, a host cell of the present disclosure does not naturally produce the desired commodity chemical, and thus contains heterologous polynucleotide constructs capable of expressing one or more genes necessary for producing the desired commodity chemical. Examples of such heterologous genes that allow host cells to produce commodity chemicals are disclosed in PCT publication WO 2010/071581 and U.S. Patent Application Publication Nos. US 2011/0068776 and US 2011/0053216.

Additionally, host cells of the present disclosure may be engineered to produce ethanol by expressing, for example, pyruvate decarboxylase (pdc) and alcohol dehydrogenase (adhB) from *Zymomonas mobilis* (or homologues thereof). Host cells of the present disclosure may also be engineered to produce isobutyraldehyde by expressing, for example, 2-acetolactate synthase (alsS) from *Bacillus subtilis*, acetohydroxy acid isomeroreductase (ilvC) and dihydroxy acid dehydratase (ilvD) from *E. coli*, and 2-ketoisovalerate decarboxylase (kivd) from *Lactococcus lactis*. Host cells of the present disclosure may further be engineered to produce isobutanol by expressing, for example, the genes responsible for isobutyraldehyde production along with alcohol dehydrogenase (yqhD) from *E. coli*. Moreover, host cells of the present disclosure may be engineered to produce other higher order chain alcohols, such as 1-propanol, 1-butanol, 2-methyl-1-butanol, 3-methyl-1-butanol, and 2-phenylethanol, by expressing, for example, 2-ketoisovalerate decarboxylase (kivd) from *Lactococcus lactis* and alcohol dehydrogenase (yqhD) from *E. coli*.

The present disclosure also provides for isolating a commodity chemical produced from the methods of the present disclosure. Isolating the commodity chemical involves separating at least part or all of the host cells, and parts thereof, from which the commodity chemical was produced, from the isolated commodity chemical. The isolated commodity chemical may be free or essentially free of impurities formed from at least part or all of the host cells, and parts thereof. The isolated commodity chemical is essentially free of these impurities when the amount and properties of the impurities remaining do not interfere in the use of the commodity chemical.

Accordingly, in certain embodiments, a host cell of the present disclosure that recombinantly express an operon encoding the enzymes necessary for the production of shikimate and/or shikimate intermediate from phosphoenolpyruvate and erythrose-4-phosphate, and/or an operon encoding the enzymes necessary for the production of an aromatic amino acid from shikimate and/or shikimate intermediate, further contains the proteins necessary for the host cell to produce at least one commodity chemical. In certain embodiments, the host cell produces at least one commodity chemical.

Other aspects of the present disclosure relate to methods of producing at least one commodity chemical by providing a host cell containing a recombinant polynucleotide containing an operon encoding the enzymes necessary for the production of shikimate and/or shikimate intermediate from phosphoenolpyruvate and erythrose-4-phosphate, and/or a recombinant polynucleotide containing an operon encoding the enzymes necessary for the production of an aromatic amino acid from shikimate and/or shikimate intermediate; culturing the cell in a medium such that the one or more recombinant polynucleotides are expressed and at least one commodity chemical is produced; and collecting the at least one commodity chemical, where expression of the one or more recombinant polynucleotides results in increased production of shikimate, shikimate intermediate, and/or an aromatic amino acid compared to a corresponding cell lacking the one or more recombinant polynucleotides, and where the host cell contains the proteins necessary for the cell to produce the at least one commodity chemical. In some embodiments, the one or more recombinant polynucleotides are incorporated into the genome of the host cell. In other embodiments, the at least one produced commodity chemical is selected from a polymer, 1,3-propandiol, 1,4-butanediol, polyhydroxyalkanoate, polyhydroxybutyrate, isoprene, lactate, succinate, glutamate, citrate, malate, 3-hydroxypropionate, ascorbate, sorbitol, an amino acid, hydroxybutyrate, a carotenoid, lycopene, β-carotene, a pharmaceutical intermediate, a polyketide, a statin, an omega-3 fatty acid, an isoprenoid, a steroid, an antibiotic, erythromycin, a soprenoid, a steroid, erythromycin, a biofuel, and combinations thereof. In further embodiments, the produced commodity chemical is a biofuel selected from an alcohol, ethanol, propanol, isopropanol, acetone, butanol, isobutanol, 2-methyl-1-butanol, 3-methyl-1-butanol, phenylethanol, a fatty alcohol, isopentenol, an aldehyde, acetylaldehyde, propionaldehyde, butyraldehyde, isobutyraldehyde, 2-methyl-1-butanal, 3-methyl-1-butanal, phenylacetaldehyde, a fatty aldehyde, a hydrocarbon, an alkane, an alkene, an isoprenoids, a fatty acid, a wax ester, an ethyl ester, hydrogen, and combinations thereof.

It is to be understood that, while the compositions and methods disclosed herein have been described in conjunction with the preferred embodiments thereof, the foregoing description is intended to illustrate and not limit the scope thereof as defined in the appended claims. Other aspects, advantages, and modifications within the scope thereof as defined in the appended claims will be apparent to those skilled in the art to which the present disclosure pertains.

The following Example is merely illustrative and is not meant to limit any aspects of the present disclosure in any way.

EXAMPLE

Introduction

The traditional approach to improve microbial production of natural products, such as amino acids, antibiotics, etc., includes altering key structural or regulatory genes of the biosynthetic pathway followed by measuring the amount of desired product that is produced. Each change then reveals the presence or absence of a bottleneck and, based on those results, the next gene is deleted or overexpressed and the cycle repeats until product titers/yields can no longer be improved substantially. Although this step-wise approach can yield improvements in flux through these pathways, it is a tedious and time-consuming strategy, given that metabolic pathways tend to be well balanced and rarely does a single change increase flux dramatically. Indeed, some bottlenecks will not be revealed until others are relieved. This process typically leads to the identification of local yield maxima, but not the global optimal yield.

These challenges are particularly evident in efforts to engineer *Escherichia coli* to produce high yields of aromatic amino acids. With advances in metabolic engineering and discovery of novel biosynthetic pathways in plants, aromatic amino acids, which have been important commodities used as animal feeds, food additives, and supplements, can also serve as precursors to a variety of commercially valuable molecules and pharmaceutical drugs (13, 42). Recently, several publications used L-tyrosine over-producing strains of *Escherichia coli* grown on glucose to produce biopolymer starting materials such as p-hydroxycinnamic acid and p-hydroxystyrene (29, 39, 40), and drug precursors such as reticuline, an important intermediate in biosyntheses of benzylisoquinoline alkaloids (29, 39, 40). Yet, of the three aromatic amino acids derived from the shikimate pathway, the L-tyrosine yield is the lowest, ranging from approximately 0.10 to approximately 0.15 g per g glucose (Table 1). Though Patnaik et al. recently reported L-tyrosine titers of over 50 g/L using *E. coli* in a 200-L bioreactor by improving the fermentation and isolation steps (35), the production strain only yielded ~0.10 gram of L-tyrosine per gram of glucose (33). Further improvement in the yield is needed to make the process as economically competitive as the processes used to synthesize other amino acids, such as L-lysine, L-glutamate, and L-alanine (17, 21).

In these previous studies, gene expression was modified for only a few candidates of the L-tyrosine pathway at a time, and a large number of strains had to be screened to circumvent bottlenecks. The following example demonstrates the construction of a strain that harbored all of the genes necessary for the production of L-tyrosine on two plasmids (11 genes in total). This strain was analyzed for L-tyrosine production, pathway enzyme levels, and intermediates. The results were used to identify multiple bottlenecks, and to engineer subsequent strains for improved production of specific enzymes. By applying these techniques over several rounds of engineering L-tyrosine production was significantly improved from 20% to 80% of the theoretical yield (0.44 g L-tyrosine/g glucose) without resorting to time- and resource-consuming characterization of the complete pathway gene expression landscape.

Materials and Methods

PCR Amplification of Genes and Construction of Plasmids

TABLE 1

L-Tyrosine production yields from various *E. coli* strains engineered within the past ten years

| Strain | Genotype | Titer (g/L) | $Y_{tyr/glu}$ (g/g) | %-$Y_t$ | Ref. |
|---|---|---|---|---|---|
| DPD4193 | K-12, aroH367, tyrR366, tna-2, lacY5, malT384, aroG397(fbr), trpE382, Ptrc-tyrA :: KanR, ΔpheLA | 0.18 (55) | 0.09 | 16 | (33, 35) |
| T2 | K-12, ΔtyrR, pCL1920 :: $P_{LtetO-1}$-aroG$^{fbr}$-tyrA$^{fbr}$-ppsA-tktA | 0.62 (9.7) | 0.124 | 22 | (26) |
| T2-YK | K-12, ΔtyrR, pCL1920 :: $P_{LtetO-1}$-aroG$^{fbr}$-tyrA$^{fbr}$-ppsA-tktA, pBR322 :: $P_{LtetO-1}$-aroK-ydiB | 0.70 | 0.14 | 25 | (25) |
| PB12CP | JM101, Δ(ptsHI crr), Glc$^+$, pJLB::aroG$^{fbr}$, pTrc :: tyrC-pheA$_{CM}$ | 0.18 (3) | 0.064 | 12 | (6) |
| ygdT KO | K-12, ΔpheA, ΔtyrR, ygdT::kan, pCL1920 :: tyrA$^{fbr}$-aroG$^{fbr}$ | 0.59 | 0.118 | 21 | (38) |

For Table 1, the reported titers and yields were results from shake flask cultures, except those in parenthesis which were from bioreactors. All cultures were grown at 37° C., except for PB12CP which was grown at 30° C. The theoretical yield (%-$Y_t$) was calculated based on the maximum value of 0.55 g of L-tyrosine per g of glucose (43).

Despite a vast wealth of literature accumulated over the past thirty years pertaining to the enzymatic activities and expression properties of the shikimate pathway, it remains difficult to engineer (4, 13, 14, 17, 42). Previous L-tyrosine engineering work has most often focused on the transcriptional deregulation of the tyrR and/or trpR regulons, followed by removing the feedback inhibition on two key enzymes, 3-deoxy-D-arabino-heptulosonate (DAHP) synthase (AroG), which catalyzes the first committed step to the shikimate pathway, and the dual function chorismate mutase/prephenate dehydrogenase (TyrA), which catalyzes the first two steps in L-tyrosine biosynthesis from chorismate (26, 33). Co-expression of the rate-limiting enzymes, shikimate kinase (AroK or AroL) and quinate/shikimate dehydrogenase (YdiB), and deletion of the L-phenylalanine branch of the aromatic amino acid biosynthetic pathway have been shown to increase the L-tyrosine production (12, 25, 33). Furthermore, overexpression of phosphoenolpyruvate synthase (PpsA) and transketolase A (TktA), altering glucose transport and use of other carbon sources, such as xylose and arabinose, have also been shown to increase the precursor pools to the shikimate pathway (1, 9, 22, 26, 34, 47, 48).

All genes (open reading frames) were amplified by PCR from the genomic DNA of *E. coli* MG1655 and extended with 5'-AAAGGAGGCCATCC-3' (SEQ ID NO:1) at the 5'-end, and with the corresponding endonuclease restriction sites at the 5'- and 3'-ends of the fragments. The feedback-resistant mutants, aroG* [D146N] and tyrA* [M53I;A354V] (26), were obtained using the technique of rapid PCR site-directed mutagenesis (45). To improve the expression of AroB, rare codons found within the first 15 codons were optimized, as shown in bold: ATG GAG CGT ATT GTC GTT ACT CTG GGC GAA CGT AGC TAC CCA ATT (SEQ ID NO:2), yielding aroB$^{op}$, the codon-optimized variant of aroB.

Figure 2:
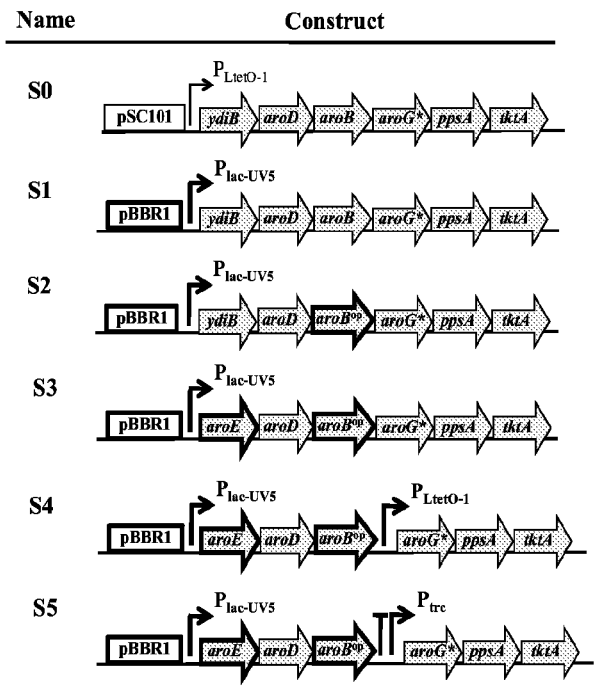
FIG. 2A depicts stepwise improvements of the shikimate module by changing the origin of replication from pSC101 to pBBR1, and the promoter from $P_{LtetO-1}$ to $P_{lac-UV5}$ (S1), followed by codon optimization of aroB (S2), substitution of ydiB with aroE (S3), and insertion of a second promoter $P_{LtetO-1}$ 5' of aroG* (S4). In S5, a combination of the rrnB terminator T1 (symbol T) and $P_{trc}$ was used to substitute $P_{LtetO-1}$ 5' of aroG*, which resulted in significant reduction in protein and shikimate production.
FIG. 2B depicts SRM results indicating the relative levels of TktA through YdiB/AroE as the consequence of the various modifications to the shikimate module.
Figure 2:
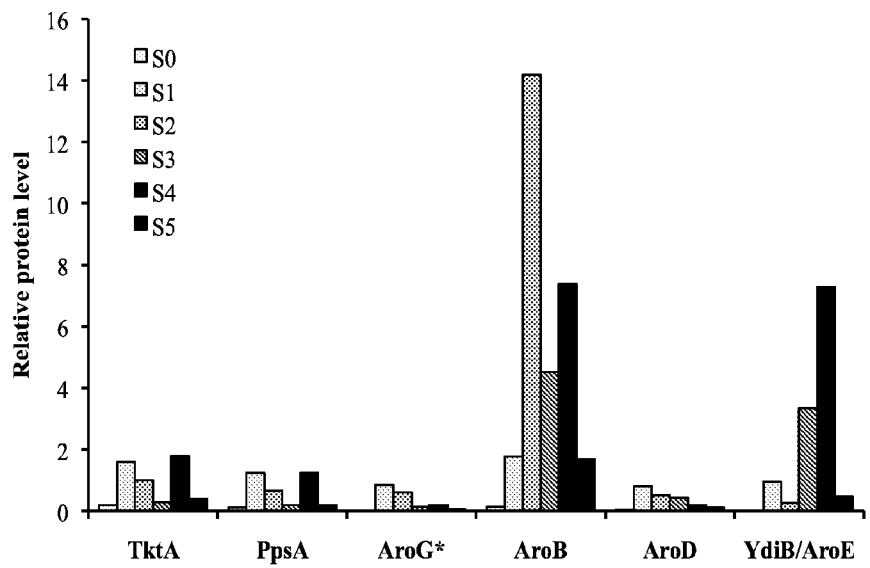
Figure 3:
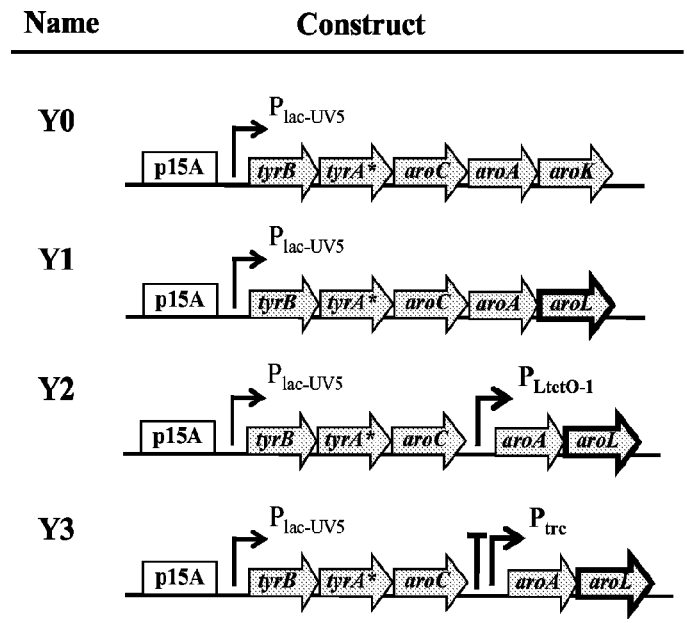
FIG. 3A depicts stepwise improvements of the tyrosine module by substitution of aroK with aroL (Y1), and insertion of a second promoter, either $P_{LtetO-1}$ (Y2) or a combination of the rrnB terminator T1 (symbol T) and $P_{trc}$ (Y3), 5' of aroA.
FIG. 3B depicts SRM results indicating the relative levels of TyrB through AroL as the consequence of the various modifications to the tyrosine module.
Figure 3:
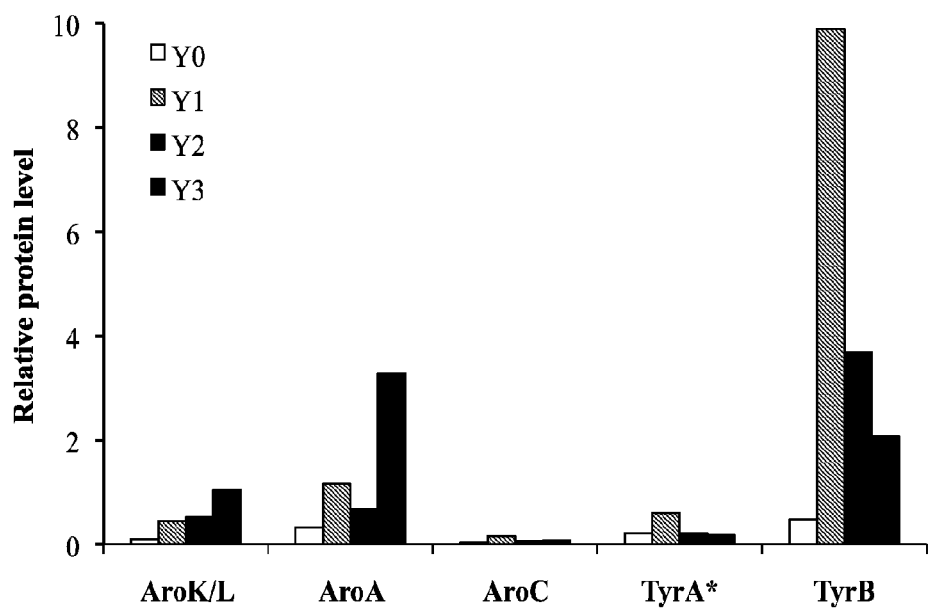

The L-tyrosine biosynthetic pathway (central metabolites to L-tyrosine) was encoded in several variants of two modules: the shikimate module and the tyrosine module. The shikimate modules encode the enzymes that transform pyruvate, F6P, and G3P into shikimate, and versions of this module containing various plasmid origins, gene variants, promoters, and transcription terminators are referred to as S0 to S5, and are harbored on plasmids pS0 to pS5 (FIGS. 1 and 2). The tyrosine modules encode the enzymes that transform shikimate into L-tyrosine, and versions of this module containing various gene variants, promoters, and transcription terminators are referred to as Y0 to Y3, and are harbored on plasmids pY0 to pY3 (FIGS. 1 and 3).

For construction of the initial shikimate module S0 (Table 2), the fragment containing ydiB, aroD, and aroB, with an EcoRI restriction site at the 5'-end and combined NheIxxx- BamHI restriction sites at the 3'-end, was constructed using SOE-PCR (15), and cloned into pZS21 (27) between the EcoRI and BamHI restriction sites. The genes that encode the enzymes that produce DAHP from pyruvate, F6P, and G3P (aroG*, ppsA, and tktA) were cloned into pPro33 (20). The fragment containing 5'-aroG*-XbaI-ppsA-NdeI-tktA-3', a DAHP-expressing operon, was amplified and extended by PCR with the NheI and BamHI restriction sites at the 5'- and 3'-ends, respectively; it was inserted at the 3'-end of aroB between the NheI and BamHI sites creating plasmid pS0.

TABLE 2

List of plasmids used

| Plasmid | Description |
|---|---|
| | Base plasmids |
| pZS21 | pSC101, Kan$^R$, P$_{LtetO-1}$ |
| pZA31 | p15A, Cm$^R$, P$_{LtetO-1}$ |
| pBbB5c | pBBR1, Cm$^R$, lacI, P$_{lac-UV5}$ |
| pRBS01 | p15A, Amp$^R$, P$_{lac-UV5}$ |
| pBbA5a | p15A, Amp$^R$, lacI, P$_{lac-UV5}$ |
| | Shikimate Plasmids |
| pS0 | pZS21 :: ydiB-aroD-aroB-aroG*-ppsA-tktA |
| pS1 | pBbB5c :: ydiB-aroD-aroB-aroG*-ppsA-tktA |
| pS2 | pBbB5c :: ydiB-aroD-aroB$^{op}$-aroG*-ppsA-tktA |
| pS3 | pBbB5c :: aroE-aroD-aroB$^{op}$-aroG*-ppsA-tktA |
| pS4 | pBbB5c :: aroE-aroD-aroB$^{op}$, P$_{LtetO-1}$-aroG*-ppsA-tktA |
| pS5 | pBbB5c :: aroE-aroD-aroB$^{op}$, T1-P$_{trc}$-aroG*-ppsA-tktA |
| | Tyrosine Plasmid |
| pY0 | pRBS01 :: tyrB-tyrA*-aroC-aroA-aroK |
| pY1 | pRBS01 :: tyrB-tyrA*-aroC-aroA-aroL |
| pY2 | pBbA5a :: tyrB-tyrA*-aroC, P$_{LtetO-1}$-aroA-aroL |
| pY3 | pBbA5a :: tyrB-tyrA*-aroC, T1-P$_{trc}$-aroA-aroL |
| | Other plasmids |
| pDHQ | pZA31 :: aroB-aroG*-ppsA-tktA |
| pDHS | pZA31 :: aroD-aroB-aroG*-ppsA-tktA |

In Table 2 above, the parental plasmids pZS21 and pZA31 were previously described (27). Descriptions for pRBS01 and pBb-plasmids are available at the JBEI registry (JBEI Registry website). The copy number determined for pBBR1 and p15A ori in pBbB5c and pBbA5a are listed in the registry; they range from 8 to 10, and 17 to 20 copies per cell, respectively. Asterisks in aroG* and tyrA* refer to the feedback resistant variants of aroG and tyrA, respectively. aroB$^{op}$ is the codon-optimized variant of aroB. T1 is the *E. coli* rrnB terminator t1. It precedes P$_{trc}$ to prevent run through by the first promoter.

Because some of the intermediates in the biosynthetic pathway cannot be purchased to use as standards for analysis, strains were engineered that could produce these intermediates. Two plasmids, pDHQ and pDHS, were constructed using pZA31 (27), which only differences from pZS21 are its replication origin (p15A versus pSC101) and resistance marker (chloramphenicol versus kanamycin) (Table 2), to produce standards for the measurement of the metabolic intermediates involved in the hydroaromatic equilibrium. The DHQ operon is essentially S0 without ydiB-aroD; when pDHQ transformed into cells, those cells accumulate dehydroquinate (DHQ). The DHS operon is essentially S0 without ydiB; when pDHS transformed into cells, those cells accumulate dehydroshikimate (DHS).

For construction of the plasmids harboring the tyrosine modules Y0 (pY0) and Y1 (pY1) (Table 2), plasmid pRBS01 (JBEI Registry website) was used as the backbone. Two fragments, the first containing tyrB and tyrA* and the second containing aroC and aroA, were assembled using PCR-SOEing (15). They were cloned between BglII and HindIII of the plasmid as 5'-BglII-tyrB-tyrA*-XhoI-aroC-aroA-KpnI-HindIII-3'. Subsequently, either aroK or aroL was cloned between the KpnI and HindIII sites to produce pY0 or pY1, respectively (Table 2).

Construction of Biobrick Operons

The remaining shikimate and tyrosine plasmids (pS1 to pS5, and pY2 to pY3) were constructed using the Bglbrick standard and plasmids pBbB5c and pBbA5a (3), which are described in the JBEI registry (JBEI Registry website). For each ORF to be cloned into these BglBrick plasmids, all EcoRI, BglII, BamHI, and XhoI restriction sites within the sequence were removed by codon substitution. The ORFs were then amplified by PCR with primers that extended the 5'- and 3'-ends with EcoRIxxBglII and BamHIxxXhoI, respectively. Positions xx are the adenylate dinucleotides (AA) but can be any random sequence. Similar to the other ORFs in this study, all genes contained the consensus 5'-AGGAGG-3' ribosome binding site followed by a spacer sequence 5'-CCATCC-3' (41). Prior to cloning, all PCR fragments were digested with BglII and XhoI, and then inserted into the corresponding plasmid stepwise, starting from the 5'-end to the 3'-end, replacing the original insert, gfp or rfp, respectively.

In brief, pS1 replaces the pSC101 origin and the promoter P$_{LtetO-1}$ on pS0 with the pBBR1 origin and P$_{lac}$-V5, respectively. pS2 replaces aroB on pS1 with its codon-optimized variant aroB$^{op}$. pS3 replaces ydiB on pS2 with aroE. pS4 adds to pS3 an additional promoter, P$_{LtetO-1}$, between aroB$^{op}$ and aroG*. pS5 adds to pS3 a transcription terminator and P$_{trc}$ between aroB$^{op}$ and aroG*. For the tyrosine plasmids, pY2 adds the promoter P$_{LtetO-1}$ between aroC and aroA on pY1. pY3 adds a transcription terminator and P$_{trc}$ between aroC and aroA on pY1.

*E. coli* Strains and Culture Conditions

All plasmid manipulations were performed using the *E. coli* DH10B strain, unless otherwise stated. For shikimate and L-tyrosine production data, *E. coli* MG1655 was used and cultured in 50 mL MOPS-M9 minimal medium containing 0.5% glucose (31) and supplemented with the appropriate amount of antibiotics: carbenicillin at 100 µg/mL, chloramphenicol at 30 µg/mL, and/or kanamycin at 50 µg/mL. All cultures were grown at 37° C. in a 250 mL shake flask with shaking at 200 rpm. For induction, 50 µM of 1 mM IPTG was added into the culture after 3 h of incubation time. Samples used to analyze L-tyrosine and shikimate levels were collected at 24 hours; except for Strain F sample, which were also collected at 48 hours (see Table 3 below).

HPLC Measurements for L-Tyrosine Production

L-Tyrosine titers were measured using HPLC with UV detection. A 500 µL aliquot of culture was drawn and diluted into 1 N HCl, followed by incubation at 55° C. for 30 min with occasional vortexing. The sample was then centrifuged, and the collected supernatant was diluted further with the appropriate amount of water prior to injection into an Agilent 1200 Series HPLC system equipped with a photodiode array detector set at 210, 254, and 280 nm (Agilent Technologies, Santa Clara, Calif.). The separation was achieved with a reverse phase C$_{18}$ column (Inertsil 2.1×250 mm, 3.5 µm, from GL Sciences, Inc., Torrance, Calif.) at a flow rate of 0.15 mL/min. L-Tyrosine was eluted with a linear gradient of water (A) and methanol (B) as follows: 5% B from 0-8 minutes, 5-40% B from 8-13 minutes, hold at 40% B from 13-16 minutes, 40-5% B from 16-21 minutes, and finally allow the column to equilibrate at 5% B for 10 minutes. L-Tyrosine from *E. coli* extracts was quantified using a five-point calibration curve ranging from 14 mg/L to 448 mg/L. The $R^2$ coefficient for the L-tyrosine calibration curve was 0.99.

Targeted Proteomics Analysis

The levels of enzymes in the L-tyrosine biosynthetic pathway were determined using single reaction monitoring (SRM) mass spectrometry. After 24 hours of cultivation, cells were pelleted by centrifugation and the supernatant was discarded. Protein extraction, alkylation, digestion, and analysis were performed as previously described (36). Briefly, the protein was extracted from the cell pellet by using chloroform-methanol precipitation and resuspended in 10% methanol for total protein quantification via the DC Protein reagent (BioRad, Hercules, Calif.). Fifty μg of protein was reduced with 5 mM tris(2-carboxyethyl)phosphine, subsequently alkylated with 200 mM iodoacetic acid, and digested overnight at 37° C. by using trypsin at a ratio of 1:50 trypsin:sample. Prior to LC-MS analysis, bovine serum albumin digest was added at a concentration of 17 fmol/μL to serve as an internal standard.

Protein samples were analyzed using an Eksigent TEMPO nanoLC-2D coupled to an AB Sciex 4000 Q-Trap mass spectrometer running with Analyst™ 1.5 operating in SRM mode. Samples were loaded onto a PepMap100 μ-guard column (Dionex-LC Packings) and washed (20 mins, 15 μL/min) with buffer A (2% (v/v) acetonitrile, 0.1% (v/v) formic acid, balance $H_2O$). Samples were eluted over a Pepmap100 analytical column (75 mm i.d., 150 mm length, 100 Å, 3 mm) with a 15-minute gradient from 5% to 30% buffer B (98% (v/v) acetonitrile, 0.1% formic acid, balance $H_2O$). Following peptide elution, the column was washed at 80% buffer B for 10 minutes, and allowed to equilibrate for 13 minutes at 5% buffer B prior to the next analysis.

Three unique peptide transitions were chosen and optimized for each protein encoded on the tyrosine and shikimate modules. Each peptide transition was verified by using full MS/MS scans and subsequent database searching to confirm that the correct peptide was selected. MultiQuant™ version 1.2 and 2.0 software (AB Sciex) was used to determine the peak area for each transition. Sample load variations were normalized by using the antibiotic markers specific to each plasmid and the BSA internal standard.

Analysis of Pathway Intermediates

All pathway intermediates were quantified using HPLC-ESI-TOF MS. For quantification of anionic, non-phosphorylated metabolites, 1 mL of culture was mixed with ice-cold methanol (1:1, v/v), and de-proteinated by filtration (YM-3 centrifuge filter, Millipore Inc., Billerica, Mass.). For phosphorylated intracellular metabolites, cells from the 50-mL culture were collected by centrifugation and extracted with 0.5 mL of ice-cold methanol followed by 0.5 mL of ice-cold water. The samples were then dried by lyophilization (Labconco Co., Kansas City, Mo.), reconstituted in 0.5 mL water-methanol (1:1 v/v), and protein was removed as above.

All chemical standards were purchased from Sigma-Aldrich and prepared as a 100-μM stock solution in methanol-water (50:50, v/v). The standards for dehydroquinate (DHQ) and dehydroshikimate (DHS), which were produced using *E. coli* engineered with the pathway ending at these metabolic intermediates, were purified via an Agilent 1200 Series preparative LC system and a Carbomix® H-NP 10:8% preparative column (21.2×300 mm, 10 μm, Sepax Technologies, Inc., Newark, Del.).

The separation of metabolites was conducted on the Fermentation-monitoring HPX-87H column with 8% cross linkage (150 mm length, 7.8 mm internal diameter, and 9 μm particle size; Bio-Rad, Richmond, CA, USA) using an Agilent Technologies 1100 Series HPLC system. A sample injection volume of 10 μL was used throughout. The sample tray and column compartment were set to 4 and 50° C., respectively. Metabolites were eluted isocratically with a mobile phase composition 0.1% formic acid in water at a flow rate of 0.5 mL/min.

The HPLC system was coupled to an Agilent Technologies 6210 Series time-of-flight mass spectrometer (LC-TOF MS) via MassHunter workstation (Agilent Technologies, CA, USA). Drying and nebulizing gases were set to 13 L/min and 30 psi, respectively, and a drying gas temperature of 330° C. was used throughout. Electrospray ionization (ESI) was conducted in the negative ion mode and a capillary voltage of −3500 V was utilized. All other MS conditions were mentioned elsewhere (11). Metabolites from *E. coli* extracts were quantified via seven-point calibration curves ranging from 625 nM to 50 μM. The $R^2$ coefficients for the calibration curves were ≥0.99.

Results

Initial Pathway Construction

The L-tyrosine biosynthetic genes (FIG. 1A) were assembled into two modules, one containing six genes for the production of shikimate from erythrose-4-phosphate (E4P) and phosphoenolpyruvate (PEP), and another containing five genes for the final production of L-tyrosine from shikimate. The *E. coli* strain MG1655 was selected as the production host rather than strains that have been engineered to overproduce L-tyrosine, as MG1655 is a genetically unmodified strain that is better suited for analyzing the performance of the engineered synthetic system described herein. It was determined that the basal levels of proteins and metabolites in the L-tyrosine biosynthetic pathway in *E. coli* MG1655 were negligible as compared to those produced by our modular system.

The L-tyrosine production pathway was divided into two modules at the intermediate shikimate, rather than at chorismate, which is the natural branch point in the shikimate pathway (8), for several reasons. First, chorismate is unstable at 37° C., which would make optimization of a partial pathway ending at chorismate more difficult. Moreover, splitting the pathway at chorismate would require the first nine genes to be cloned into one plasmid, while splitting at shikimate required the cloning of only the first six genes into the first plasmid, which was easier and faster to accomplish. Additionally, shikimate is stable in liquid culture and is commercially valuable as a precursor in the synthesis of Tamiflu® (19).

Previous studies have made advances in engineering the L-tyrosine pathway (24-26), which provided useful information from which to build the modular system described herein. In their initial constructs, Liitke-Eversloh and Stephanopoulos (2007) achieved an L-tyrosine production of 0.621±0.026 g/L (26) by over-expressing aroG* [D146N], tyrA* [M53I;A354V], ppsA, and tktA on a pSC101 plasmid under the control of a constitutive promoter ($P_{LtetO-1}$ with no tetR) in the tyrR knockout strain; following combinatorial analysis, production was increased by ~26% when the isozymes YdiB and AroK were additionally co-expressed on a pBR322 plasmid (25). Utilizing this work as a starting point, pZS21 (27) was selected. The pZS21 construct contains the pSC101 origin of replication and $P_{LtetO-1}$ to express the genes of the first shikimate module (S0) creating plasmid pS0. The pRBS01 (JBEI Registry website) construct was also selected, as it contains a medium copy number plasmid with a p15A origin of replication and the IPTG-inducible $P_{lac-UV5}$ to express the genes of the first tyrosine module (Y0), creating plasmid pY0.

Moreover, YdiB (instead of AroE) was selected as the dehydrogenase for production of shikimate, and AroK (instead of AroL) was selected as the shikimate kinase in the first set of operons (FIG. 1B and Table 2). All of the genes in the operons were initially ordered such that the last gene in the metabolic pathway was placed closest to the promoter, and so on. Experimental observations showed that genes close to the promoter are generally induced at much higher rates than those distal from the promoter. Without wishing to be bound by theory, it is believed that this reverse arrangement would create a metabolic flux pull towards the product by increasing protein concentration of the enzymes occurring in the latter part of the pathway. Under the production conditions described herein, Strain A, harboring pS0 and pY0, yielded 0.746±0.018 g/L L-tyrosine (Table 3), consistent with previous studies (25, 26). When the orientation of the genes in the modules S0 or Y0 were reversed, the production dropped significantly to about 0.180 g/L in either case. Changes of this magnitude in product titer resulting from reversing the order of genes in the operon have been reported previously (2). In their construction of the taxadiene biosynthetic pathway, Ajikumar et al. (2010) observed that when the order of the genes of the geranyl geranyl pyrophosphate synthase (GGPS) and taxadiene synthase (TS) was reversed in the operon, opposite to the sequence of the reaction mechanism, the production increased by two to three-fold.

TABLE 3

L-Tyrosine production of the various strains constructed in this study

| Strain | Plasmids | Titer (g/L) | $g_{Tyr}/g_{CDW}$ | %-$Y_t$ |
|---|---|---|---|---|
| A | pS0 and pY0 | 0.746 ± 0.018 | 0.921 ± .022 | 27 |
| B | pS0 and pY1 | .897 ± 0.028 | 0.944 ± .029 | 33 |
| C | pS4 and pY1 | 1.15 ± 0.028 | 1.31 ± .032 | 42 |
| D | pS5 and pY1 | 1.22 ± 0.024 | 1.45 ± .029 | 44 |
| E | pS4 and pY2 | 0.908 ± 0.005 | 0.987 ± 0.005 | 33 |
| F | pS4 and pY3 | 2.17 ± 0.382 | 2.64 ± 0.466 | 79 |
| G | pS5 and pY3 | 1.31 ± 0.075 | 1.62 ± 0.093 | 48 |

For Table 3, the basal strain was *E. coli* MG1655, which was transformed with the various shikimate and L-tyrosine plasmids (Table 2). The reported L-tyrosine titer in g/L was the final production obtained within 24 hours when glucose had been completely consumed, with the exception of Strain F (which was 48 hours), in a 50 mL MOPS-M9 minimal medium shake flask culture containing 5 g/L glucose, shaken at 200 rpm and 37° C. For Strain F, the L-tyrosine titer at 24 hour was 1.51±0.027 g/L. All cultures were induced with 50 µM IPTG, except for that of Strain A. For Strain A, the production maximized at 1 mM IPTG. $g_{Tyr}/g_{CDW}$ is the L-tyrosine production in g per gram of dry cell weight. The average dry cell weight for all of the strains was 0.38 g/L per OD of culture density; it is consistent with the value reported previously (6).

Analysis of Pathway Enzyme and Intermediate Levels

In order to rapidly identify pathway bottlenecks in Strain A, LC-MS-based analysis of pathway enzymes and intermediates was performed. From targeted proteomics analysis, the protein levels in the shikimate module were unchanged between the induced and uninduced samples because expression was constitutive, under the control of $P_{LtetO-1}$ with no $tet^R$ (FIG. 1C). In contrast, the genes in the tyrosine module were expressed under the control of the inducible promoter $P_{lac}$-UV5, and strong induction of protein production by IPTG was observed (FIG. 1C). However, the amount of increase in the protein level decreased the further away the ORF was located from the promoter (i.e., 14-fold increase in TyrB, while only a two-fold increase in AroK, the protein product from the final gene in the operon). Consistent with the plasmid copy number, enzymes in the shikimate module were produced at lower levels relative to those in the tyrosine module. The targeted proteomics results indicated that YdiB and AroB were produced at very low levels, suggesting that they would be good targets for subsequent engineering efforts.

To complement the targeted proteomic analysis, the levels of each of the pathway intermediates in Strain A were analyzed, along with the precursors E4P and PEP. An LC-ESI-TOF MS approach was used to identify the intermediates and precursors based on their retention time and accurate mass measurements. Results from the metabolite analysis (Table 4) showed an accumulation of intermediates preceding AroK in the pathway: shikimate (SHIK), dehydroshikimate (DHS), dehydroquinate (DHQ), and the side product quinate (QUIN) (FIG. 1A), which occurred due to the quinate dehydrogenase activity of YdiB (28). Knop et al. reported the hydroaromatic equilibrium between these intermediates and quinate (18), thus reducing flux to shikimate and downstream metabolites. There was no other significant accumulation of pathway intermediates. These data, along with the proteomic analysis, show that there is at least one bottleneck between AroB and AroK in the pathway.

TABLE 4

Hydroaromatic equilibrium and intermediate levels (mg/L) accumulated in *E. coli* MG1655 harboring various shikimate modules constructs

| Module | QUIN | DHQ | DHS | SHIK |
|---|---|---|---|---|
| S0 | 106 ± 1 | 36 ± 1 | 588 ± 13 | 79 ± 2 |
| S1 | 165 ± 1 | 51 ± 1 | 1029 ± 6 | 194 ± 2 |
| S2 | 242 ± 4 | 56 ± 1 | 1227 ± 65 | 278 ± 28 |
| S3 | 2 ± 0 | 5 ± 0 | 70 ± 6 | 510 ± 18 |
| S4 | 3 ± 1 | 8 ± 0 | 113 ± 3 | 759 ± 39 |
| S5 | 11 ± 1 | 4 ± 0 | 46 ± 4 | 273 ± 20 |

For Table 4, an equilibrium was shown to exist between shikimate (SHIK) and the two preceding intermediates, dehydroquinate (DHQ) and dehydroshikimate (DHS), and the side product quinate (QUIN) whose formation is catalyzed by YdiB (28). It occurs right after the formation of DAHP, and prior to the formation of the shikimate 3-phosphate, the first intermediate in the tyrosine module (FIG. 1A). The hydroaromatic levels were determined following the conditions in Table 3

Optimization of the Shikimate Module

From the above proteomic analysis, it was shown that a significant improvement to shikimate flux through the pathway was achieved by making improvements to the protein levels encoded on the shikimate plasmid. Since the levels of YdiB and AroB were very low, and intermediates produced or consumed by these enzymes were also accumulated, these proteins were targeted for further engineering. To increase protein levels and address the bottlenecks leading to the conversion of shikimate to shikimate-3-phosphate catalyzed by AroK, a new plasmid (pS1) was constructed by cloning the shikimate biosynthetic genes from pS0 into pBbB5c (JBEI Registry website), which has a higher copy origin of replication (FIG. 2A; Table 2). Metabolite analysis of the shikimate pathway intermediates for the strain harboring pS1 showed production of 194±2 mg/L of shikimate, which is a greater than 100% increase in shikimate production as compared to the original construct pS0 (Table 4). However, production of the precursors DHQ and DHS, as well as the side product QUIN, were also increased by about 100% as well (Table 4). Moreover, when SRM analysis was performed to determine protein production from the new plasmid, neither modification to the plasmid (i.e., increasing copy number or promoter strength) improved YdiB or AroB levels significantly (FIG. 2B), which only compounded the problems associated with metabolic flux to shikimate.

Since multiple attempts to modify the plasmid construct did not improve YdiB and AroB levels, the gene sequences were modified directly. Analysis of the aroB nucleotide sequence revealed several rare codons at the beginning of the gene. Thus, to improve aroB expression, the first fifteen codons were optimized by removing the rare codons (16, 44), generating aroB$^{op}$, which was used to construct pS2 (FIG. 2A and Table 2). Targeted proteomic analysis indicated that codon optimization of aroB improved the production of the AroB enzyme (FIG. 2B). Additionally, shikimate pathway metabolite analysis showed increased accumulation of the downstream metabolites DHQ, DHS, and SHIK (Table 4). However, the bottleneck at YdiB remained. Thus, YdiB was replaced with the isoenzyme AroE (5) in the pS3 plasmid (FIG. 2A). Subsequent protein analysis indicated that aroE produced much more protein than ydiB (FIG. 2B). Moreover, metabolite analysis indicated that AroE did not favor the formation of quinate (Table 4), which is consistent with its specificity for shikimate (5, 28). Compared to the original shikimate module (in S0), shikimate production using pS3 increased approximately 5-fold (Table 4). Nevertheless, the total flux through S3 decreased, as compared to the YdiB-containing modules S1 and S2, which is believed to be due to feedback inhibition of AroE by shikimate (7, 18), and the recently proposed AroE-catalyzed production of gallic acid from dehydroshikimate (30).

To determine whether any new bottlenecks were created by the above engineering efforts, the genes of the shikimate module (aroE, aroD, aroB, aroG*, ppsA, and tktA) were individually expressed on pBbB5c in a strain that also harbored the shikimate module S0 (on pS0) and tyrosine module Y1 (on pY1) (see Strain B in Table 3). In this case, L-tyrosine production relative to the two-plasmid strain was measured (Table 5). The results indicated that the first three enzymes in the pathway (aroG*, ppsA, and tktA) were rate-limiting steps, and that increasing even one of these enzymes at a time yielded a greater than 14% improvement in L-tyrosine production (Table 5). Interestingly, these three genes (aroG*, ppsA, and tktA) catalyze the formation of pathway precursors PEP and E4P, and the first committed intermediate in the pathway, DAHP (FIG. 1A).

TABLE 5

Combinatorial analysis of the shikimate module for improving L-tyrosine production in Strain B.

| Plasmid co-expressed | % improvement |
| --- | --- |
| pBbB5c :: ydiB | 4.4 ± 0.2 |
| pBbB5c :: aroE | 9.9 ± 0.6 |
| pBbB5c :: aroD | 10.9 ± 0.7 |
| pBbB5c :: aroB$^{op}$ | 3.4 ± 0.2 |
| pBbB5c :: aroG | 33.5 ± 1.6 |
| pBbB5c :: tktA | 20.2 ± 1.1 |
| pBbB5c :: ppsA | 14.5 ± 1.0 |

In order to increase the expression of aroG*, ppsA, and tktA on the shikimate module S3, two different promoters were inserted 5' of aroG* to increase the levels of the three genes furthest from the promoter (FIG. 2A). When the constitutive P$_{LtetO-1}$ was inserted 5' of aroG* (S4), shikimate production increased by 50% (Table 4). However, proteomic analysis indicated that the production of PpsA and TktA, but not of AroG* were increased when compared to expression from pS3 (FIG. 2B). When a regulated P$_{trc}$ preceded by an E. coli rrnB T1-terminator, which prevents read through from the first promoter, was inserted 5' of aroG* (pS5), the shikimate titer decreased by about 46±4% (Table 4). It is believed that this occurred because protein production from the module decreased uniformly by a factor of approximately 4-fold (FIG. 2B). Moreover, expression decreased with increasing IPTG concentration.

Optimization of the Tyrosine Module and Production Analysis

Based on the improvements observed with increasing protein levels for the shikimate module, a similar approach was used to improve expression of AroA and AroK at the end of the operon in the tyrosine module (FIG. 3A). First the expression of AroK was increased, as its protein level was relatively low compared to that of the other four enzymes in the operon (FIG. 1C). Moreover, AroK catalyzes the conversion of shikimate to shikimate-3-phosphate (S3P), which is known to be a rate-limiting step (25). However, repeated attempts to insert a second promoter 5' of the gene or to modify the RBS of aroK was unsuccessful, which is believed to be due to plasmid instability as reported previously for an aroK-containing plasmid (37).

Consequently, it was decided to replace AroK with AroL, as AroL has a higher affinity for shikimate than does AroK (46). Substitution of aroL for aroK in the original tyrosine plasmid (pY1 for pY0) yielded about 0.900 g/L of L-tyrosine, which is an increase of 20% when compared to pY0 (Strain B; Table 3). The substitution also resulted in higher cell density, and as such the ratio of g$_{Tyr}$/g$_{CDW}$ for Strains A and B did not significantly differ (Table 3). Interestingly, the use of AroL in Strain B eliminated the accumulation of shikimate and other metabolites involved in the hydroaromatic equilibrium. Moreover, proteomic analysis indicated that protein levels in the aroL-containing pY1 were higher than those in the aroK-containing pY0 (FIG. 3B). These results suggest that a major bottleneck existed at AroK in the original L-tyrosine producing strain. Additionally, when pY1 was co-transformed with the best shikimate-producing plasmid, pS4, the L-tyrosine titer increased by 28% to 1.15 g/L (Table 3) indicating that improvements in metabolic flux to shikimate yielded a significant impact on L-tyrosine production.

To further improve L-tyrosine production, two different promoters were inserted after the third ORF, aroC, on the tyrosine plasmid, to increase expression of aroA and aroL. As with the shikimate plasmid, first P$_{LtetO-1}$ was inserted between aroC and aroA, creating pY2. When pY2 was transformed into cells harboring pS4, only 0.908 g/L of L-tyrosine was produced after 24 hours (Table 3), which indicates that addition of the second promoter reduced L-tyrosine production compared to the strain harboring pS4 and pY1. Proteomic analysis suggested that this decreased production occurred due to a reduction in AroA production, despite the additional promoter, and also TyrB, TyrA*, and AroC, in the preceding operon (FIG. 3B).

A second double-operon tyrosine plasmid (pY3) was constructed to incorporate an E. coli rrnB T1-terminator 5' of P$_{trc}$, which is 5' of aroA. This resulted in the production of over twice as much AroL and more than five times as much AroA in cells harboring pY3 compared to cells harboring pY2 (FIG. 3B). However, AroC levels remained quite low, and TyrB and TyrA* decreased even further.

When the pY3 plasmid was transformed into cells harboring pS4, a titer of 1.5 g/L of L-tyrosine was obtained after 24 hours of growth and 2.17±0.382 g/L L-tyrosine after 48 hours of growth (Table 3). This was significantly higher than that of the single-operon plasmid (Table 3). This titer corresponds to an overall yield of 0.44 g L-tyrosine/g glucose fed, which is approximately 80% of the theoretical yield (Table 3). This 0.44 g L-tyrosine/g glucose fed represents an increase of approximately 254% over the previously obtained 0.124 g L-tyrosine/g glucose fed (Table 1). The increase in L-tyrosine production caused by the increase in AroA and AroL expression in pY3, despite lower amounts of AroC, TyrA*, and TyrB, indicated that both AroA and AroL are rate-limiting enzymes in the lower half of the L-tyrosine biosynthetic pathway.

Furthermore, the results show that as compared to the previously obtained 0.70 g/mL titer yield of L-tyrosine production (Table 1), the titer yield of Strain A was approximately 6.5% greater, the titer yield of Strain B was approximately 28% greater, the titer yield of Strain C was approximately 64% greater, the titer yield of Strain D was approximately 74% greater, the titer yield of Strain E was approximately 30% greater, the titer yield of Strain F was approximately 210% greater, and the titer yield of Strain G was approximately 87% greater.

The results also show that as compared to the previously obtained 25% theoretical yield of L-tyrosine production (Table 1), the theoretical yield from Strain A was approximately 8% greater, the theoretical yield from Strain B was approximately 32% greater, the theoretical yield from Strain C was approximately 68% greater, the theoretical yield from Strain D was approximately 76% greater, the theoretical yield from Strain E was approximately 32% greater, the theoretical yield from Strain F was approximately 216% greater, and the theoretical yield from Strain G was approximately 92% greater.

Discussion

The results described herein show that an efficient L-tyrosine production system has been constructed using *E. coli* engineered to contain two modules that convert central metabolic intermediates into L-tyrosine. Expression of the genes in the tyrosine modules was optimized using various replication origins, promoters, transcription terminators, and gene and enzyme variants, and using two LC-MS technologies to elucidate the levels of enzymes and metabolic intermediates in the biosynthetic pathway. In contrast to previous studies, all of the genes in the L-tyrosine production pathway were recombinantly expressed, rather than only expressing a selective few targets. Using LC-MS-based targeted proteomics and metabolite profiling, the levels of all of the pathway enzymes and intermediates were monitored simultaneously, allowing for the quick identification of bottlenecks and adjustment of gene expression to optimize the metabolic flux for the production of L-tyrosine. This resulted is a modular production system, containing two dual-operon plasmid-based modules, each of which were optimized to express shikimate and L-tyrosine, respectively. Compared to previous strategies, which selectively chose one or two genes to modify on the chromosome or plasmid, the modular system developed herein is far more versatile because it can be used in any host strain, and the BglBrick operons constructed can be used as building blocks to generate other shikimate- or L-tyrosine-related biosynthetic pathways.

The results of the analysis described herein unambiguously revealed several bottlenecks of the shikimate pathway that were not previously known, and led to the engineering of a system that significantly increased L-tyrosine production to 80% of the theoretical yield. Metabolite profiling indicated that dehydroquinate (DHQ), dehydroshikimate (DHS), and shikimate (SHIK) accumulated in the initial strain, suggesting that the main bottleneck in the first part of the pathway was due to YdiB. Efforts to increase YdiB levels improved shikimate production. However, the levels of DHQ and DHS also increased proportionally. These data support previous observations that YdiB possesses both quinate and shikimate dehydrogenase activities (10, 23), and that the hydroaromatic equilibrium between DHQ, DHS, SHIK, and the side product quinate, limits production of shikimate and downstream metabolites. The molar ratio of DHQ, DHS, SHIK, and QUIN, calculated from the amounts expressed by all of the shikimate modules containing YdiB (pS0 to pS3) was 1.0:21.4:4.0:3.4. When aroE was substituted for ydiB, quinate was not detected significantly in the culture, and DHS was efficiently converted to SHIK. The molar ratio between DHS and SHIK calculated from pS3 through pS5 was 1:7.

Potential loss in the metabolic flux due to the feedback inhibition of AroE by shikimate and formation of gallic acid (7, 30) was also avoided by replacing aroK with aroL on the plasmids containing the L-tyrosine pathway. Previously, it has been shown that overexpression of AroK is better than AroL at increasing L-tyrosine production (25). However, limitations from YdiB could have precluded any improvements from AroL. The metabolite analysis presented above shows that the highest amount of L-tyrosine production from that system (~0.700 g/L) could be limited due to inefficient conversion to shikimate even if high levels of YdiB are present.

SRM analysis of protein levels also provided valuable insight into gene expression from both plasmids. The SRM data for the initial constructs (FIG. 1C) were consistent with previous experimental observation that the genes farther away from the promoter are induced to a lesser extent by IPTG as compared to those closer to the promoter. Thus, insertion of a second promoter in the plasmid following the first three genes improved protein production from the genes 3' of the promoter. However, inserting $P_{LtetO-1}$ alone, without a terminator 5' of the promoter, did not increase the production of the protein encoded by the gene directly following that promoter; the second and third genes following the promoter were expressed at a higher level, as is evident in both the shikimate and tyrosine modules S4 and Y1. Inserting a trc promoter, with an *E. coli* rrnB T1-terminator 5' of the promoter to prevent read-through, increased production of AroA and AroL in the tyrosine module, but also resulted in a general repression of the genes in the shikimate module S5.

It is interesting to note that the production data and SRM analysis described herein are consistent with a previous study in which pulse-feeding experiments and statistical analysis identified AroB, AroA, and AroL as promising metabolic engineering targets for alleviating flux control in L-phenylalanine-producing strains (32). In this study, it was demonstrated that using the shikimate operons, resulted in AroB expression that remained relatively low unless its first fifteen codons were optimized. Additionally, it was shown that when using the tyrosine production module, the large increase in L-tyrosine production only occurred when expression of AroA and AroL were up-regulated by insertion of T1-$P_{trc}$ 5' of aroAL in the tyrosine module Y3. As compared to the tyrosine module without the second promoter (Y1), L-tyrosine production doubled in strains harboring pY3, when used in conjunction with the plasmid (pS4) that harbors shikimate module S4. Nevertheless, the AroC level was relatively low in all constructs tested, suggesting that further improvements may be achieved by increasing AroC levels.

With all the improvements that were made to the shikimate pathway in the two bi-operon modules, an L-tyrosine yield of 0.44 g/g glucose was successfully achieved, which is approximately 80% of the theoretical yield of L-tyrosine from glucose (43). The techniques used to optimize L-tyrosine biosynthesis pathway, such as targeted proteomics and metabolite profiling, may be readily applied to the biosynthesis of L-phenylalanine, L-tryptophan, and other complex metabolic pathways.

REFERENCES

1. Ahn, J. O., H. W. Lee, R. Saha, M. S. Park, J. K. Jung, and D. Y. Lee. 2008. Exploring the effects of carbon sources on the metabolic capacity for shikimic acid production in *Escherichia coli* using in silico metabolic predictions. J Microbiol Biotechnol 18:1773-1784.
2. Ajikumar, P. K., W. H. Xiao, K. E. Tyo, Y. Wang, F. Simeon, E. Leonard, O. Mucha, T. H. Phon, B. Pfeifer, and G. Stephanopoulos. 2010. Isoprenoid pathway optimization for Taxol precursor overproduction in *Escherichia coli*. Science 330:70-74.
3. Anderson, J. C., J. E. Dueber, M. Leguia, G. C. Wu, J. A. Goler, A. P. Arkin, and J. D. Keasling. 2010. BglBricks: A flexible standard for biological part assembly. J Biol Eng 4:1.
4. Bongaerts, J., M. Kramer, U. Muller, L. Raeven, and M. Wubbolts. 2001. Metabolic engineering for microbial production of aromatic amino acids and derived compounds. Metab Eng 3:289-300.
5. Chaudhuri, S., and J. R. Coggins. 1985. The purification of shikimate dehydrogenase from *Escherichia coli*. Biochem J 226:217-223.
6. Chavez-Bejar, M. I., A. R. Lara, H. Lopez, G. Hernandez-Chavez, A. Martinez, O. T. Ramirez, F. Bolivar, and G. Gosset. 2008. Metabolic engineering of *Escherichia coli* for L-tyrosine production by expression of genes coding for the chorismate mutase domain of the native chorismate mutase-prephenate dehydratase and a cyclohexadienyl dehydrogenase from *Zymomonas mobilis*. Appl Environ Microbiol 74:3284-3290.
7. Dell, K. A., and J. W. Frost. 1993. Identification and removal of impediments to biocatalytic synthesis of aromatics from D-glucose: rate-limiting enzymes in the common pathway of aromatic amino acid biosynthesis. Journal of the American Chemical Society 115:11581-11589.
8. Dosselaere, F., and J. Vanderleyden. 2001. A metabolic node in action: chorismate-utilizing enzymes in microorganisms. Crit Rev Microbiol 27:75-131.
9. Draths, K. M., D. L. Pompliano, D. L. Conley, J. W. Frost, A. Ilerry, G. L. Disbrow, R. J. Staversky, and J. C. Lievense. 1992. Biocatalytic Synthesis of Aromatics from D-Glucose—the Role of Transketolase. Journal of the American Chemical Society 114:3956-3962.
10. Duncan, K., S. Chaudhuri, M. S. Campbell, and J. R. Coggins. 1986. The overexpression and complete amino acid sequence of *Escherichia coli* 3-dehydroquinase. Biochem J 238:475-483.
11. Eudes, A., E. E. Baidoo, F. Yang, H. Burd, M. Z. Hadi, F. W. Collins, J. D. Keasling, and D. Loque. 2011. Production of tranilast [N-(3',4'-dimethoxycinnamoyl)-anthranilic acid] and its analogs in yeast *Saccharomyces cerevisiae*. Appl Microbiol Biotechnol 89:989-1000.
12. Gavini, N., and L. Pulakat. 1991. Role of translation of the pheA leader peptide coding region in attenuation regulation of the *Escherichia coli* pheA gene. J Bacteriol 173:4904-4907.
13. Gosset, G. 2009. Production of aromatic compounds in bacteria. Curr Opin Biotechnol 20:651-658.
14. Herrmann, K. M., and L. M. Weaver. 1999. The Shikimate Pathway. Annu Rev Plant Physiol Plant Mol Biol 50:473-503.
15. Horton, R. M., H. D. Hunt, S. N. Ho, J. K. Pullen, and L. R. Pease. 1989. Engineering hybrid genes without the use of restriction enzymes: gene splicing by overlap extension. Gene 77:61-68.
16. Humphreys, D. P., M. Sehdev, A. P. Chapman, R. Ganesh, B. J. Smith, L. M. King, D. J. Glover, D. G. Reeks, and P. E. Stephens. 2000. High-level periplasmic expression in *Escherichia coli* using a eukaryotic signal peptide: importance of codon usage at the 5' end of the coding sequence. Protein Expr Purif 20:252-264.
17. Ikeda, M. 2006. Towards bacterial strains overproducing L-tryptophan and other aromatics by metabolic engineering. Appl Microbiol Biotechnol 69:615-626.
18. Knop, D. R., K. M. Draths, S. S. Chandran, J. L. Barker, R. von Daeniken, W. Weber, and J. W. Frost. 2001. Hydroaromatic equilibration during biosynthesis of shikimic acid. J Am Chem Soc 123:10173-10182.
19. Kramer, M., J. Bongaerts, R. Bovenberg, S. Kremer, U. Muller, S. Orf, M. Wubbolts, and L. Raeven. 2003. Metabolic engineering for microbial production of shikimic acid. Metab Eng 5:277-283.
20. Lee, S. K., and J. D. Keasling. 2005. A propionate-inducible expression system for enteric bacteria. Appl Environ Microbiol 71:6856-6862.
21. Leuchtenberger, W., K. Huthmacher, and K. Drauz. 2005. Biotechnological production of amino acids and derivatives: current status and prospects. Appl Microbiol Biotechnol 69:1-8.
22. Li, K., and J. W. Frost. 1999. Microbial synthesis of 3-dehydroshikimic acid: a comparative analysis of D-xylose, L-arabinose, and D-glucose carbon sources. Biotechnol Prog 15:876-883.
23. Lindner, H. A., G. Nadeau, A. Matte, G. Michel, R. Menard, and M. Cygler. 2005. Site-directed mutagenesis of the active site region in the quinate/shikimate 5-dehydrogenase YdiB of *Escherichia coli*. J Biol Chem 280:7162-7169.
24. Lutke-Eversloh, T., C. N. Santos, and G. Stephanopoulos. 2007. Perspectives of biotechnological production of L-tyrosine and its applications. Appl Microbiol Biotechnol 77:751-762.
25. Lutke-Eversloh, T., and G. Stephanopoulos. 2008. Combinatorial pathway analysis for improved L-tyrosine production in *Escherichia coli*: identification of enzymatic bottlenecks by systematic gene overexpression. Metab Eng 10:69-77.
26. Lutke-Eversloh, T., and G. Stephanopoulos. 2007. L-tyrosine production by deregulated strains of *Escherichia coli*. Appl Microbiol Biotechnol 75:103-110.
27. Lutz, R., and H. Bujard. 1997. Independent and tight regulation of transcriptional units in *Escherichia coli* via the LacR/O, the TetR/O and AraC/I1-I2 regulatory elements. Nucleic Acids Res 25:1203-1210.

28. Michel, G., A. W. Roszak, V. Sauve, J. Maclean, A. Matte, J. R. Coggins, M. Cygler, and A. J. Lapthorn. 2003. Structures of shikimate dehydrogenase AroE and its Paralog YdiB. A common structural framework for different activities. J Biol Chem 278:19463-19472.
29. Minami, H., J. S. Kim, N. Ikezawa, T. Takemura, T. Katayama, H. Kumagai, and F. Sato. 2008. Microbial production of plant benzylisoquinoline alkaloids. Proc Natl Acad Sci USA 105:7393-7398.
30. Muir, R. M., A. M. Ibanez, S. L. Uratsu, E. S. Ingham, C. A. Leslie, G. H. McGranahan, N. Batra, S. Goyal, J. Joseph, E. D. Jemmis, and A. M. Dandekar. 2011. Mechanism of gallic acid biosynthesis in bacteria (*Escherichia coli*) and walnut (*Juglans regia*). Plant *Mol Biol* 75:555-565.
31. Neidhardt, F. C., P. L. Bloch, and D. F. Smith. 1974. Culture medium for enterobacteria. J Bacteriol 119:736-747.
32. Oldiges, M., M. Kunze, D. Degenring, G. A. Sprenger, and R. Takors. 2004. Stimulation, monitoring, and analysis of pathway dynamics by metabolic profiling in the aromatic amino acid pathway. Biotechnol Prog 20:1623-1633.
33. Olson, M. M., L. J. Templeton, W. Suh, P. Youderian, F. S. Sariaslani, A. A. Gatenby, and T. K. Van Dyk. 2007. Production of L-tyrosine from sucrose or glucose achieved by rapid genetic changes to phenylalanine-producing *Escherichia coli* strains. Appl Microbiol Biotechnol 74:1031-1040.
34. Patnaik, R., and J. C. Liao. 1994. *Engineering of Escherichia coli central metabolism for aromatic metabolite production with near theoretical yield*. Appl Environ Microbiol 60:3903-3908.
35. Patnaik, R., R. R. Zolandz, D. A. Green, and D. F. Kraynie. 2008. L-tyrosine production by recombinant *Escherichia coli*: fermentation optimization and recovery. Biotechnol Bioeng 99:741-752.
36. Redding-Johanson, A. M., T. S. Batth, R. Chan, R. Krupa, H. L. Szmidt, P. D. Adams, J. D. Keasling, T. Soon Lee, A. Mukhopadhyay, and C. J. Petzold. 2011. Targeted proteomics for metabolic pathway optimization: Application to terpene production. Metab Eng.
37. Rood, J. I., M. K. Sneddon, and J. F. Morrison. 1980. Instability in tyrR strains of plasmids carrying the tyrosine operon: isolation and characterization of plasmid derivatives with insertions or deletions. J Bacteriol 144:552-559.
38. Santos, C. N., and G. Stephanopoulos. 2008. Melanin-based high-throughput screen for L-tyrosine production in *Escherichia coli*. Appl Environ Microbiol 74:1190-1197.
39. Sariaslani, F. S. 2007. Development of a combined biological and chemical process for production of industrial aromatics from renewable resources. Annu Rev Microbiol 61:51-69.
40. Sato, F., T. Inui, and T. Takemura. 2007. Metabolic engineering in isoquinoline alkaloid biosynthesis. Curr Pharm Biotechnol 8:211-218.
41. Shine, J., and Dalgarno, L. 1974. *The 3'-terminal sequence of Escherichia coli 16S ribosomal RNA: complementarity to nonsense triplets and ribosome binding sites*. Proc Natl Acad Sci USA 71:1342-1346.
42. Sprenger, G. A. 2007. From scratch to value: engineering *Escherichia coli* wild type cells to the production of L-phenylalanine and other fine chemicals derived from chorismate. Appl Microbiol Biotechnol 75:739-749.
43. Varma, A., B. W. Boesch, and B. Ø. Palsson. 1993. Biochemical production capabilities of *Escherichia coli*. Biotechnol Bioeng 42:59-73.
44. Wang, H., D. J. O'Mahony, D. J. McConnell, and S. Z. Qi. 1993. Optimization of the synthesis of porcine somatotropin in *Escherichia coli*. Appl Microbiol Biotechnol 39:324-328.
45. Weiner, M. P., and G. L. Costa. 1994. Rapid PCR site-directed mutagenesis. PCR Methods Appl 4:S131-136.
46. Whipp, M. J., and A. J. Pittard. 1995. A reassessment of the relationship between aroK- and aroL-encoded shikimate kinase enzymes of *Escherichia coli*. J Bacteriol 177:1627-1629.
47. Yi, J., K. M. Draths, K. Li, and J. W. Frost. 2003. Altered glucose transport and shikimate pathway product yields in *E. coli*. Biotechnol Prog 19:1450-1459.
48. Yi, J., K. Li, K. M. Draths, and J. W. Frost. 2002. Modulation of phosphoenolpyruvate synthase expression increases shikimate pathway product yields in *E. coli*. Biotechnol Prog 18:1141-1148.

We claim:

1. A host cell comprising a recombinant polynucleotide, wherein the recombinant polynucleotide comprises an operon encoding the enzymes necessary for the production of shikimate from phosphoenolpyruvate and erythrose-4-phosphate, wherein the operon encodes an AroE enzyme or a YdiB enzyme, an AroD enzyme, an AroB enzyme, an AroG enzyme, a PpsA enzyme, and a TktA enzyme, and wherein the host cell produces shikimate in an amount greater than that of a corresponding cell lacking the recombinant polynucleotide.

2. The host cell of claim 1, wherein the genes encoding an AroE enzyme or a YdiB enzyme, an AroD enzyme, an AroB enzyme, an AroG enzyme, a PpsA enzyme, and a TktA enzyme are arranged in an order that is opposite to that of the shikimate biosynthesis mechanism.

3. The host cell of claim 1, wherein the host cell further produces dehydroshikimate, dehydroquinate, and quinate in an amount greater than that of a corresponding cell lacking the recombinant polynucleotide.

4. The host cell of claim 1, wherein the AroG enzyme comprises an Asp to Asn point mutation located at position 146 of the polypeptide sequence of the AroG enzyme.

5. The host cell of any one of claim 1, wherein the operon is operably linked to a first regulatory sequence, and wherein the operon comprises a second regulatory sequence located 5' of the gene encoding the AroG enzyme.

6. The host cell of claim 1, wherein the host cell further comprises a second recombinant polynucleotide, wherein the second recombinant polynucleotide comprises a second operon encoding the enzymes necessary for the production of an aromatic amino acid tyrosine from shikimate, wherein the second operon encodes a TyrB enzyme, a TyrA enzyme, an AroC enzyme, an AroA enzyme, and an AroL or AroK enzyme, and wherein the host cell produces tyrosine in an amount greater than that of a corresponding cell lacking the second recombinant polynucleotide.

7. The host cell of claim 6, wherein the genes encoding a TyrB enzyme, a TyrA enzyme, an AroC enzyme, an AroA enzyme, and an AroL or AroK enzyme are arranged in an order that is opposite to that of the tyrosine biosynthesis mechanism.

8. The host cell of claim 6, wherein the TyrA enzyme comprises at least one point mutation, and wherein the at least one point mutation is a Met to Ile point mutation at position 53 of the polypeptide sequence of the TyrA enzyme, or an Ala to Val point mutation at position 354 of the polypeptide sequence of the TyrA enzyme.

9. The host cell of claim 6, wherein the second operon is operably linked to a first regulatory sequence, and wherein the second operon further comprises a second regulatory sequence located after the gene encoding the AroC enzyme.

10. The host cell of claim 1, wherein the host cell further comprises a second recombinant polynucleotide, wherein the second recombinant polynucleotide comprises a second operon encoding the enzymes necessary for the production of tryptophan from shikimate, wherein the second operon encodes a TrpB or TrpA enzyme, a TrpC enzyme, a TrpD enzyme, a TrpE enzyme, an AroC enzyme, an AroA enzyme, and an AroL or AroK enzyme, and wherein the host cell produces tryptophan in an amount greater than that of a corresponding cell lacking the second recombinant polynucleotide.

11. The host cell of claim 10, wherein the genes encoding a TrpB or TrpA enzyme, a TrpC enzyme, a TrpD enzyme, a TrpE enzyme, an AroC enzyme, an AroA enzyme, and an AroL or AroK enzyme are arranged in an order that is opposite to that of the tryptophan biosynthesis mechanism.

12. The host cell of claim 1, wherein the host cell further comprises a second recombinant polynucleotide, wherein the second recombinant polynucleotide comprises a second operon encoding the enzymes necessary for the production of phenylalanine from shikimate, wherein the second operon encodes a TyrB enzyme, a PheA enzyme, an AroC enzyme, an AroA enzyme, and an AroL or AroK enzyme, and wherein the host cell produces phenylalanine in an amount greater than that of a corresponding cell lacking the second recombinant polynucleotide.

13. The host cell of claim 12, wherein the genes encoding a TyrB enzyme, a PheA enzyme, an AroC enzyme, an AroA enzyme, and an AroL or AroK enzyme are arranged in an order that is opposite to that of the phenylalanine biosynthesis mechanism.

14. The host cell of any one of claim 1, wherein the host cell further comprises proteins necessary to produce a commodity chemical.

15. The host cell of claim 1, wherein the host cell is *E. coli*.

16. A method of increasing production of a tyrosine intermediate in a host cell, the method comprising:
    a) providing the host cell of claim 1: and
    b) culturing the host cell of claim 1 in a medium such that the recombinant polynucleotide is expressed, wherein expression of the recombinant polynucleotide results in increased production of a tyrosine intermediate compared to a corresponding cell lacking the recombinant polynucleotide.

17. The method of claim 16, wherein the tyrosine intermediate is shikimate.

18. The method of claim 17, wherein the host cell produces from about 80 mg/L to about 760 mg/L of shikimate.

19. A host cell comprising:
    a first recombinant polynucleotide, wherein the first recombinant polynucleotide comprises a first operon encoding the enzymes necessary for the production of shikimate from phosphoenolpyruvate and erythrose-4-phosphate, wherein the first operon encodes an AroE enzyme, an AroD enzyme, an AroB enzyme, an AroG enzyme, a PpsA enzyme, and a TktA enzyme: and
    a second recombinant polynucleotide, wherein the second recombinant polynucleotide comprises a second operon encoding the enzymes necessary for the production of tyrosine from shikimate, wherein the second operon encodes a TyrB enzyme, a TyrA enzyme, an AroC enzyme, an AroA enzyme, and an AroL or AroK enzyme
wherein the host cell produces shikimate in an amount greater than that of a corresponding cell lacking the first recombinant polynucleotide, and wherein the host cell produces the aromatic amino acid tyrosine in an amount greater than that of a corresponding cell lacking the second recombinant polynucleotide.

20. The host cell of claim 19, wherein the genes encoding an AroE enzyme, an AroD enzyme, an AroB enzyme, an AroG enzyme, a PpsA enzyme, and a TktA enzyme are arranged in an order that is opposite to that of the shikimate biosynthesis mechanism, and wherein the genes encoding a TyrB enzyme, a TyrA enzyme, an AroC enzyme, an AroA enzyme, and an AroL or AroK enzyme are arranged in an order that is opposite to that of the tyrosine biosynthesis mechanism.

21. The host cell of claim 19, wherein the AroG enzyme comprises an Asp to Asn point mutation located at position 146 of the polypeptide sequence of the AroG enzyme.

22. The host cell of any of claim 19, wherein the first operon is operably linked to a first regulatory sequence, and wherein the first operon comprises a second regulatory sequence located 5' of the gene encoding the AroG enzyme.

23. The host cell of claim 19, wherein the TyrA enzyme comprises at least one point mutation, and wherein the at least one point mutation is a Met to Ile point mutation at position 53 of the polypeptide sequence of the TyrA enzyme, or an Ala to Val point mutation at position 354 of the polypeptide sequence of the TyrA enzyme.

24. The host cell of claim 19, wherein the second operon is operably linked to a first regulatory sequence, and wherein the second operon comprises a second regulatory sequence located after the gene encoding the AroC enzyme.

25. A method of increasing production of tyrosine in a host cell, the method comprising:
a) providing the host cell of claim 19: and
b) culturing the host cell of claim 19 in a medium such that the first and second recombinant polynucleotides are expressed, wherein expression of the first and second recombinant polynucleotides results in increased production of an aromatic amino acid tyrosine compared to a corresponding cell lacking the first and second recombinant polynucleotides.

26. The method of claim 25, wherein the host cell produces a tyrosine yield that is from about 5% to about 220% greater than an amount of tyrosine produced by the corresponding cell lacking the first and second recombinant polynucleotides.

27. The method of claim 25, wherein the tyrosine is produced at a percentage yield that is from about 27% to about 95% of the theoretical maximal yield.

* * * * *

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
aaaggaggcc atcc                                                        14

<210> SEQ ID NO 2
<211> LENGTH: 45
<212> TYPE: DNA
<213> ORGANISM: Artificial Sequence
<220> FEATURE:
<223> OTHER INFORMATION: Synthetic Construct
```

```
<400> SEQUENCE: 2
atggagcgta ttgtcgttac tctgggcgaa cgtagctacc caatt                45
```